US010675003B2

(12) United States Patent
Hiltner et al.

(10) Patent No.: US 10,675,003 B2
(45) Date of Patent: Jun. 9, 2020

(54) INTRAVASCULAR IMAGING

(71) Applicant: ACIST MEDICAL SYSTEMS, INC., Eden Prairie, MN (US)

(72) Inventors: Jason F. Hiltner, Minnetonka, MN (US); Kendall R. Waters, Livermore, CA (US); Thomas C. Moore, Livermore, CA (US)

(73) Assignee: ACIST MEDICAL SYSTEMS, INC., Eden Prairie, MN (US)

( * ) Notice: Subject to any disclaimer, the term of this patent is extended or adjusted under 35 U.S.C. 154(b) by 310 days.

(21) Appl. No.: 14/329,554

(22) Filed: Jul. 11, 2014

(65) Prior Publication Data

US 2016/0007837 A1 Jan. 14, 2016

(51) Int. Cl.
*A61B 8/08* (2006.01)
*A61B 5/00* (2006.01)
(Continued)

(52) U.S. Cl.
CPC .......... *A61B 8/5207* (2013.01); *A61B 5/0066* (2013.01); *A61B 5/0075* (2013.01);
(Continued)

(58) Field of Classification Search
CPC . A61B 8/5207; A61B 5/0084; A61B 5/02007; A61B 5/7285
See application file for complete search history.

(56) References Cited

U.S. PATENT DOCUMENTS

| | | | |
|---|---|---|---|
| 5,150,292 A * | 9/1992 | Hoffmann | A61B 6/481 250/303 |
| 7,165,010 B2 | 1/2007 | Mancini et al. | |

(Continued)

FOREIGN PATENT DOCUMENTS

| | | |
|---|---|---|
| CN | 103237503 A | 8/2013 |
| WO | 1997044089 A1 | 11/1997 |

(Continued)

OTHER PUBLICATIONS

Corretti et al., "Guidelines for the Ultrasound Assessment of Endothelial-Dependent Flow-Mediated Vasodilation of the Brachial Artery," Journal of the American College of Cardiology, vol. 39, No. 2, Jan. 2002, pp. 257-265.

(Continued)

*Primary Examiner* — Angela M Hoffa
*Assistant Examiner* — Helene Bor
(74) *Attorney, Agent, or Firm* — Fredrikson & Byron, P.A.

(57) ABSTRACT

This disclosure provides systems and methods for intravascular imaging. Some systems may be configured to generate a screening image of a section of a patient's vessel, identify one or more sub-sections of the screening image that each include a diagnostically significant characteristic of the vessel, and imaging the one or more sub-sections. Some systems may be configured to automatically identify the one or more sub-sections and/or to allow a user to manually identify the one or more sub-sections. Some systems may be configured to automatically image the one or more sub-sections after the one or more sub-sections are identified. In some examples, the system may be configured to displace blood during imaging of the sub-sections to enhance image quality. The system may be configured to minimize the period of time blood is displaced by synchronizing imaging and blood displacement.

37 Claims, 12 Drawing Sheets

(51) Int. Cl.
  *A61B 5/107* (2006.01)
  *A61B 5/02* (2006.01)
  *A61B 8/12* (2006.01)
  *A61M 5/00* (2006.01)
  *A61B 8/00* (2006.01)
(52) U.S. Cl.
  CPC ........ *A61B 5/0084* (2013.01); *A61B 5/02007* (2013.01); *A61B 5/1076* (2013.01); *A61B 5/6852* (2013.01); *A61B 5/6876* (2013.01); *A61B 5/7475* (2013.01); *A61B 8/0891* (2013.01); *A61B 8/12* (2013.01); *A61B 8/445* (2013.01); *A61B 8/5223* (2013.01); *A61M 5/007* (2013.01); *A61B 5/1079* (2013.01)

(56) References Cited

U.S. PATENT DOCUMENTS

| | | | |
|---|---|---|---|
| 7,753,852 B2 | 7/2010 | Maschke | |
| 8,412,312 B2 | 4/2013 | Judell et al. | |
| 2001/0056233 A1* | 12/2001 | Uber, III | A61B 8/06 600/431 |
| 2002/0065467 A1 | 5/2002 | Schutt | |
| 2002/0103437 A1 | 8/2002 | Jibiki | |
| 2006/0184122 A1* | 8/2006 | Nemoto | A61M 5/007 604/154 |
| 2007/0249936 A1 | 10/2007 | Deckman et al. | |
| 2008/0177139 A1 | 7/2008 | Courtney et al. | |
| 2009/0131765 A1 | 5/2009 | Roschak et al. | |
| 2009/0171201 A1 | 7/2009 | Olson | |
| 2009/0204029 A1 | 8/2009 | Kassab | |
| 2009/0234231 A1 | 9/2009 | Knight et al. | |
| 2009/0299360 A1 | 12/2009 | Ormsby | |
| 2009/0304593 A1 | 12/2009 | Frinking et al. | |
| 2010/0094133 A1 | 4/2010 | Yoshiara et al. | |
| 2010/0113887 A1* | 5/2010 | Kalafut | A61M 5/172 600/300 |
| 2010/0157041 A1* | 6/2010 | Klaiman | G06T 7/0022 348/77 |
| 2010/0168836 A1 | 7/2010 | Kassab et al. | |
| 2010/0249588 A1 | 9/2010 | Knight | |
| 2011/0071404 A1 | 3/2011 | Schmitt et al. | |
| 2011/0071405 A1* | 3/2011 | Judell | A61B 5/0066 600/479 |
| 2013/0101079 A1* | 4/2013 | Hough | A61B 6/03 378/8 |
| 2013/0216114 A1 | 8/2013 | Courtney et al. | |
| 2013/0303914 A1 | 11/2013 | Hiltner et al. | |
| 2013/0317359 A1 | 11/2013 | Wilson et al. | |
| 2014/0094691 A1* | 4/2014 | Steinberg | A61B 5/7425 600/424 |
| 2014/0180083 A1* | 6/2014 | Hoseit | A61B 5/6852 600/428 |

FOREIGN PATENT DOCUMENTS

| | | |
|---|---|---|
| WO | 1999034724 A2 | 7/1999 |
| WO | 2005070299 A1 | 8/2005 |
| WO | 2006037082 A2 | 4/2006 |
| WO | 2008042423 A2 | 4/2008 |
| WO | 2013173224 A1 | 11/2013 |
| WO | 2013177527 A1 | 11/2013 |

OTHER PUBLICATIONS

Cox et al., "Atherosclerosis Impairs Flow-Mediated Dilation of Coronary Arteries in Humans," Circulation, vol. 80, No. 3, Sep. 1989, pp. 458-465.
Jasti et al., "Correlations Between Fractional Flow Reserve and Intravascular Ultrasound in Patients with an Ambiguous Left Main Coronary Artery Stenosis," Circulation, vol. 110, 2004, pp. 2831-2836.
Kiviniemi et al., "Vasodilation of Epicardial Coronary Artery Can Be Measured With Transthoracic Echocardiography," Ultrasound in Med. & Biol., vol. 33, 2007, pp. 362-370.
Tonino et al., "Angiographic Versus Functional Severity of Coronary Artery Stenosis in the Fame Study Fractional Flow Reserve Versus Angiography in Multivessel Evaluation," Journal of American College of Cardiology, vol. 55, Jun. 2010, pp. 2816-2821.
Topol, et al., Textbook of Interventional Cardiology, 4th Edition, 2002, p. 860.
Bazilevs, Yuri et al., "From Imaging to Prediction: Emerging Non-Invasive Methods in Pediatric Cardiology," Progress in Pediatric Cardiology, Dec. 2010, pp. 81-89, vol. 30, No. 1-2, Amsterdam, The Netherlands.
Response to Written Opinion dated Aug. 13, 2014 for PCT/US2013/042676, 22 pages, sent to International Preliminary Examining Authority, European Patent Office, Rijswijk, The Netherlands dated Oct. 13, 2014.
Chapter II Demand and Response to Written Opinion dated Aug. 30, 2013 for PCT/US2013/042676, 26 pages, sent to International Preliminary Examining Authority, European Patent Office, Rijswijk, The Netherlands dated Mar. 25, 2014.
Chapter II Demand and Response to the Written Opinion dated May 27, 2014 for PCT/US2013/040765, 28 pages, sent to International Preliminary Examining Authority, European Patent Office, Rijswijk, The Netherlands dated Jul. 25, 2014.
Chen, Yan et al., "Phase Insensitive Homomorphic Imaging Processing for Speckle Reduction", Ultrasonic Imaging, Apr. 1996, vol. 18, pp. 122-139, Sage Journals, Los.
Eagle Eye® Platinum RX Digital IVUS Catheter Brochure, Volcano Corporation, San Diego, California, 2 pages.
Ledoux, Leon A.F., et al., "Angle-Independent Motion Measurement by Correlation of Ultrasound Signals Assessed with a Single Circular-Shaped Transducer," Ultrasonic Imaging, Aug. 1999, vol. 21, pp. 216-240, Sage Journals, Los Angeles, California.
Li, Xiang et al., "High-Resolution Co-Registered Intravascular Imaging with Integrated High Frequency Ultrasound and OCT Probe," 2010, pp. 1506-1509, IEEE International Ultrasonics Symposium Proceedings.
Lupotti, FA et al., "Quantitave IVUS Blood Flow using an Array Catheter", Computers in Cardiology Conference Sep. 2001, pp. 5-8, vol. 28, Rotterdam.
Notification of Transmittal of the International Preliminary Report on Patentability for PCT/US2013/040765, dated Sep. 1, 2014, 19 pages, International Preliminary Examining Authority, European Patent Office, Rijswijk, The Netherlands.
Notification of Transmittal of the International Preliminary Report on Patentability for PCT/US2013/042676, dated Nov. 4, 2014, 12 pages, International Preliminary Examining Authority, European Patent Office Rijswijk, The Netherlands.
Notification of Transmittal of the International Search Report and the Written Opinion of the International Searching Authority, or the Declaration for PCT/US2013/040765, dated Jul. 22, 2013, 13 pages, International Searching Authority, European Patent Office Rijswijk, The Netherlands.
Notification of Transmittal of the International Search Report and the Written Opinion of the International Searching Authority, or the Declaration for PCT/US2013/042676, dated Aug. 30, 2013, 14 pages, International Searching Authority, European Patent Office Rijswijk, The Netherlands.
The, S.H. et al., "Effect of Balloon Angioplasty on Femoral Artery Evaluated with Intravascular Ultrasound Imaging," 1992, pp. 483-493, vol. 86, Downloaded from http://circ.ahajournals.org/ on Dec. 24, 2013.
Wagner, Robert F. et al., "Statistics of Speckle in Ultrasound B-Scans," IEEE Transactions on Sonics and Ultrasonics, May 1983, pp. 156-163, vol. 30, No. 3.
Wang, L. M. et al., "Contrast Medium Assisted Fluid Flow Measurements," IEEE Transactions on Ultrasonics, Ferroelectrics, and Frequency Control, Mar. 1995, pp. 309-315, vol. 42, No. 2.
Webster, John G., "Measurement of Flow and Volume of Blood," Medical Instrumentation Application and Design, 2009, pp. 338-387, Wiley, 4th Edition.

(56) References Cited

OTHER PUBLICATIONS

Wilson, L.S. et al., "Measurement of Two-Dimensional Blood Velocity Vectors by the Ultrasonic Speckle Projection Technique," Ultrasonic Imaging, 1993, pp. 286-303, vol. 15.
Written Opinion for PCT/US2013/042676, dated Aug. 13, 2014, 8 pages, International Preliminary Examining Authority, European Patent Office, Rijswijk, The Netherlands.
Written Opinion for PCT/US2013/040765, dated May 25, 2014, 7 pages, International Preliminary Examining Authority, European Patent Office, Rijswijk, The Netherlands.
Xu, Tiantian, "Two Dimensional Blood Flow Velocity Estimation using Ultrasound Speckle Pattern Dependence on Scan Direction and Velocity," Biological Systems Engineering at DigitalCommons@University of Nebraska—Lincoln, Aug. 1, 2012 Dissertation, 169 pages.
Notification of Transmittal of the International Search Report and the Written Opinion of the International Searching Authority, or the Declaration for PCT/US2014/046374, dated Mar. 27, 2015, 13 pages, International Searching Authority, European Patent Office Rijswijk, The Netherlands.
International Patent Application No. PCT/US2014/046374, International Preliminary Report on Patentability dated Oct. 4, 2016, 20 pages.

* cited by examiner

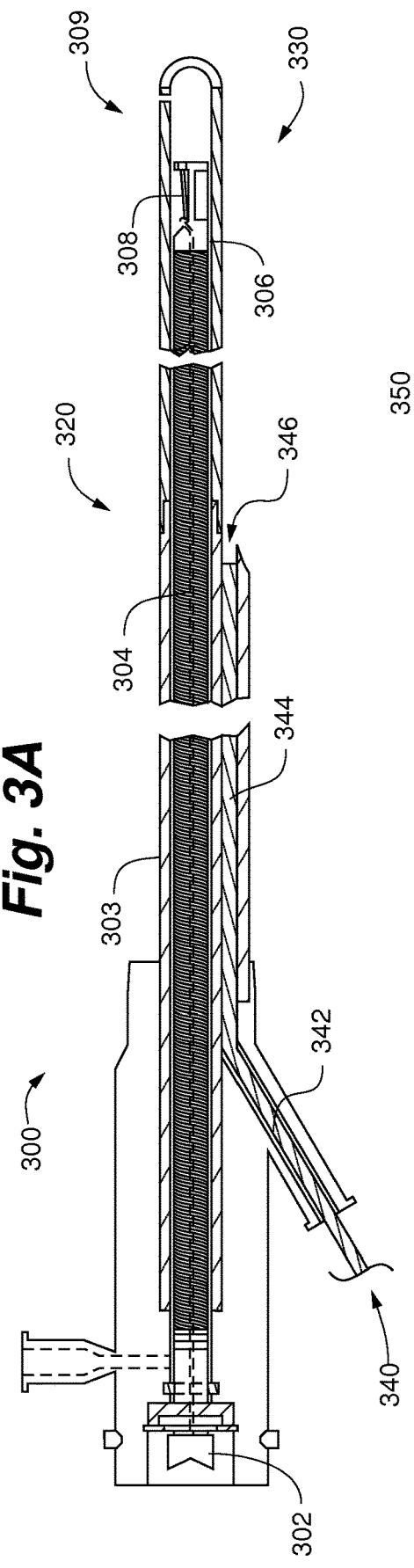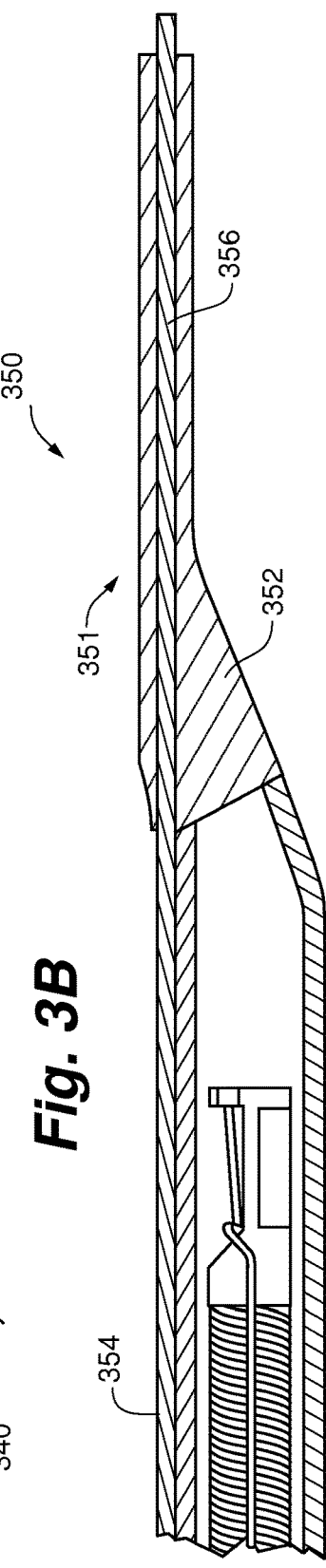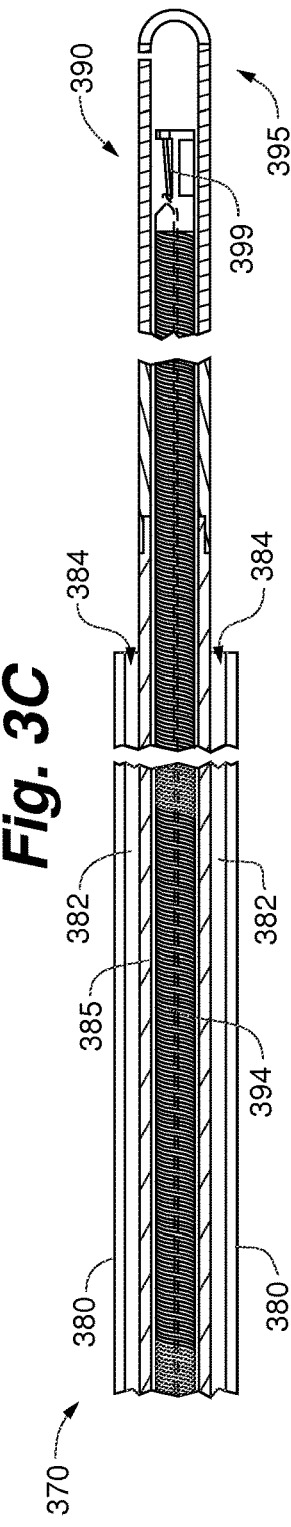

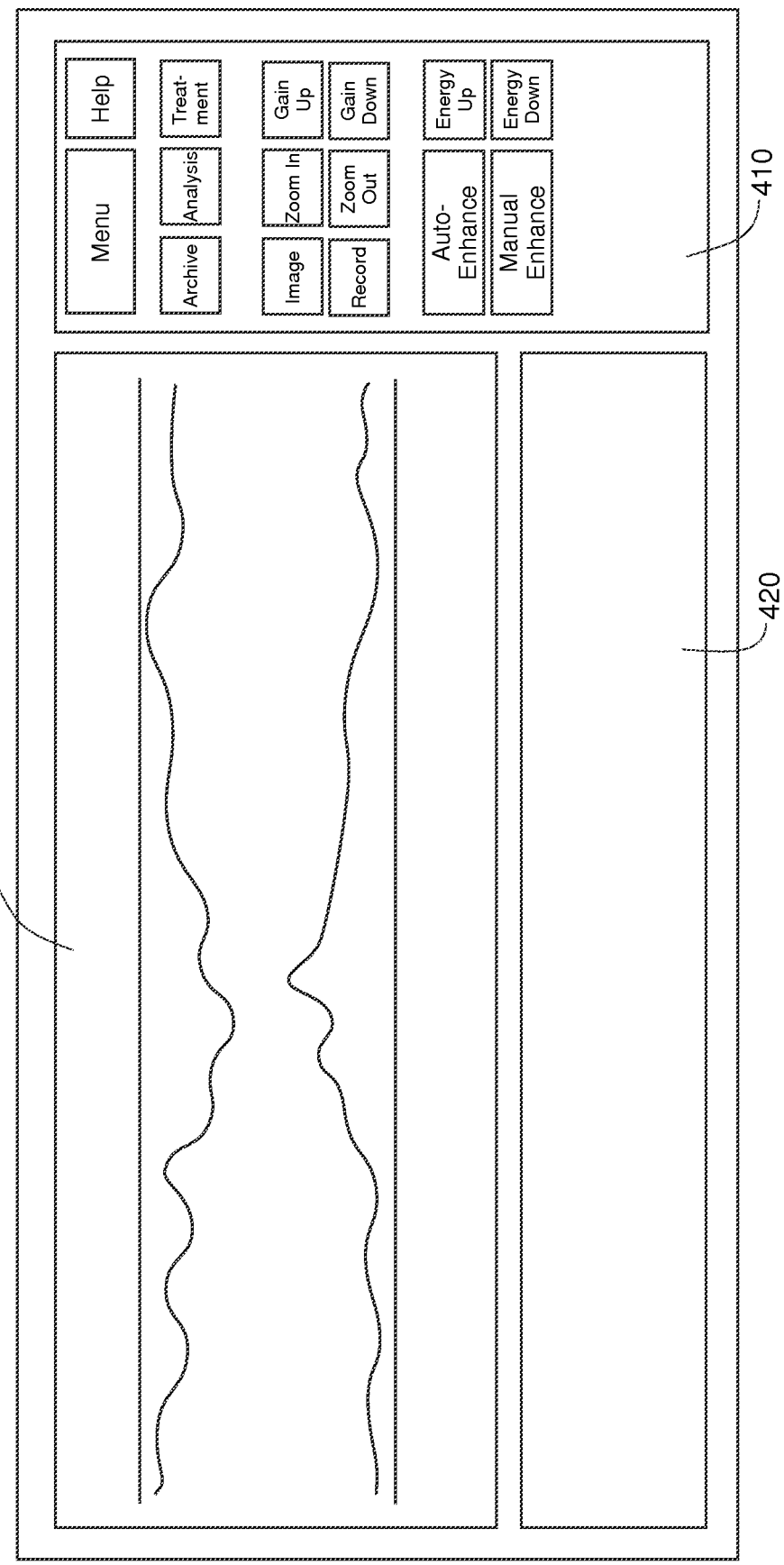

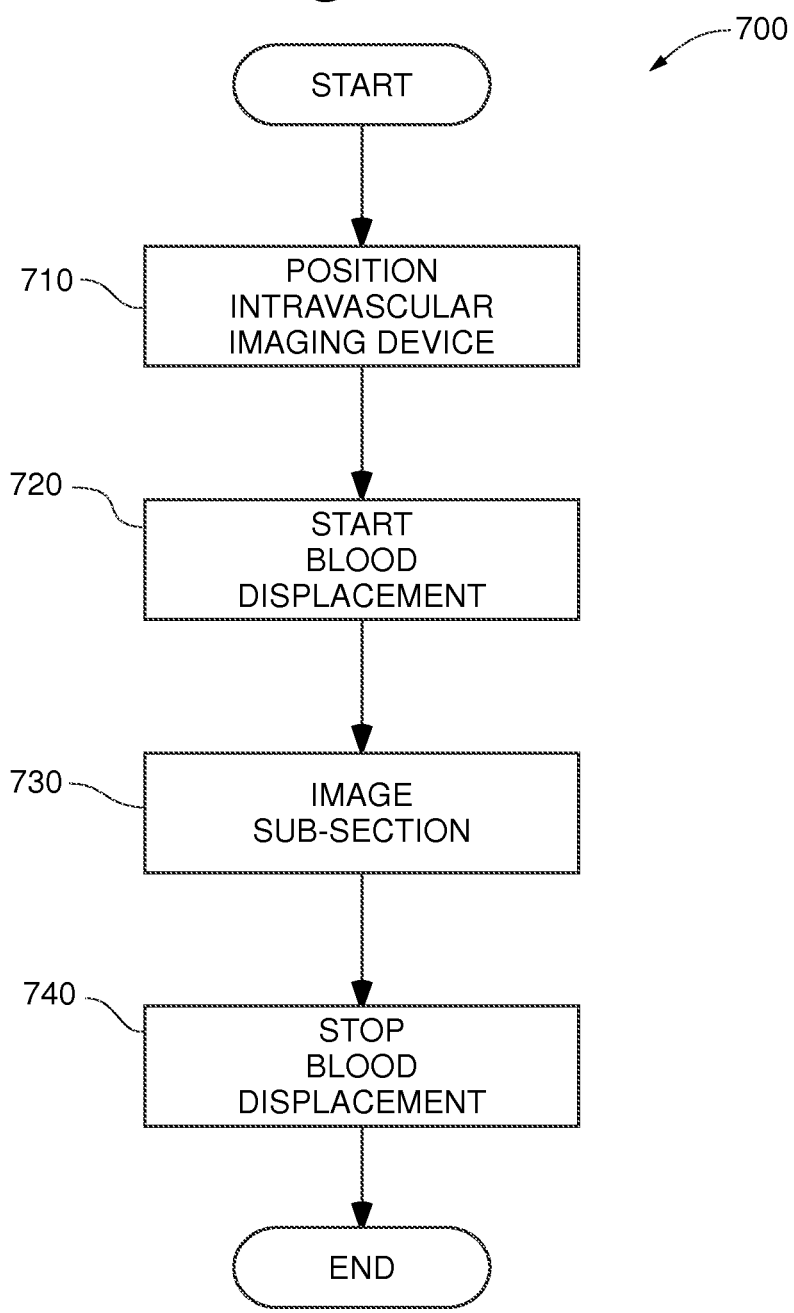

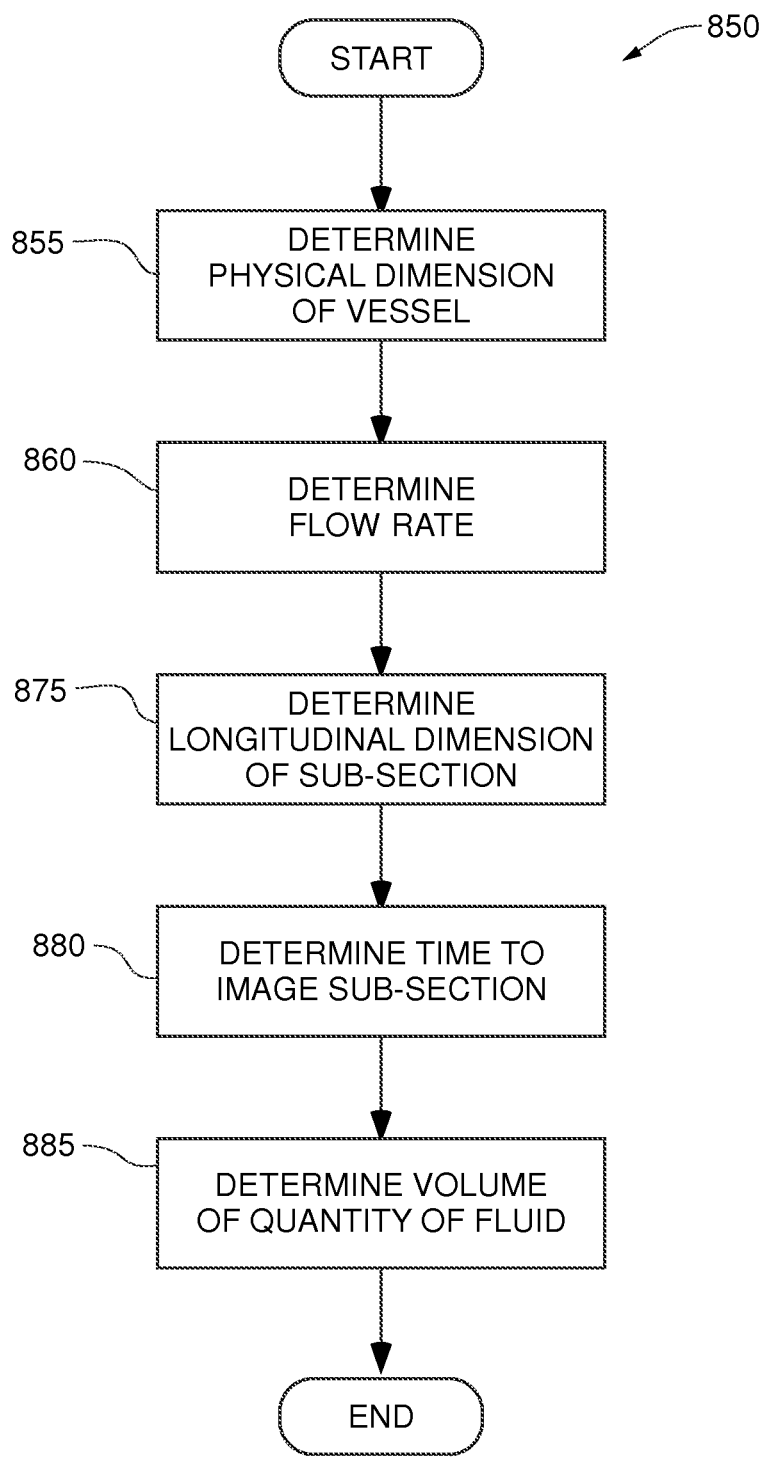

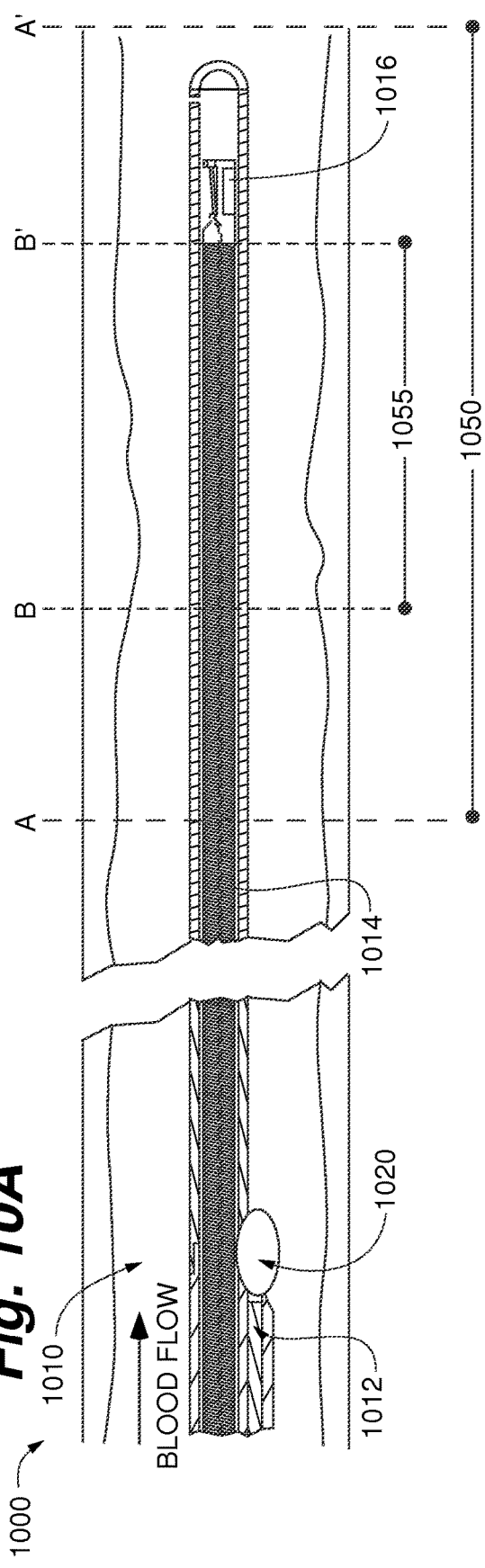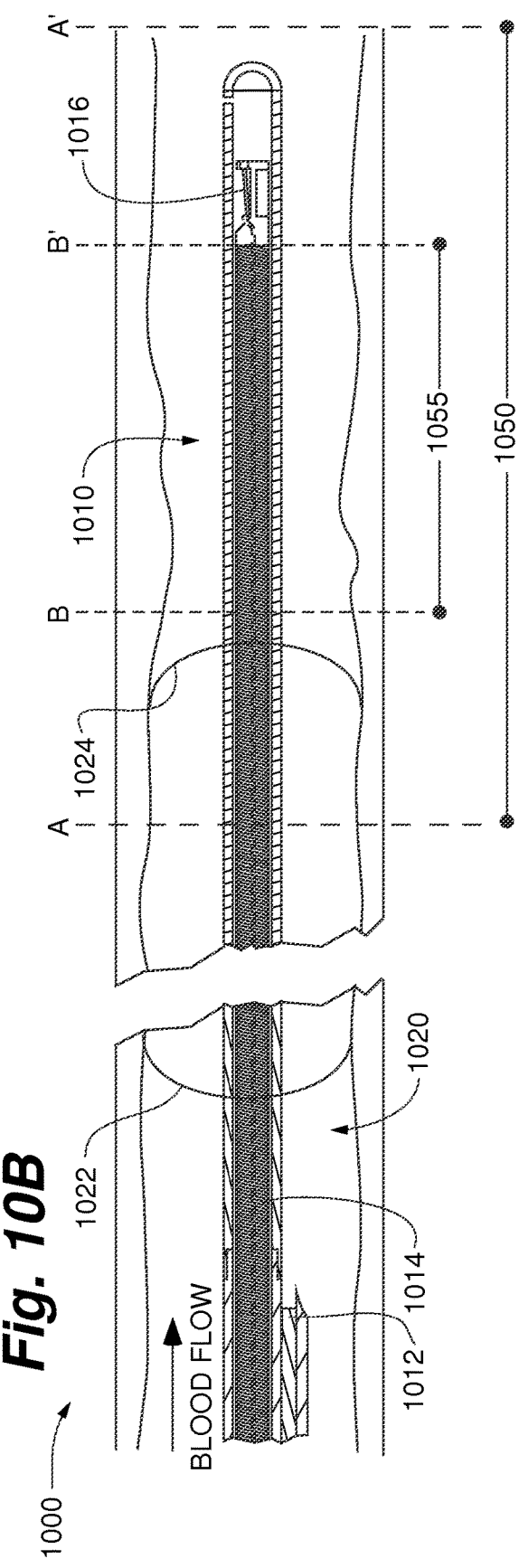

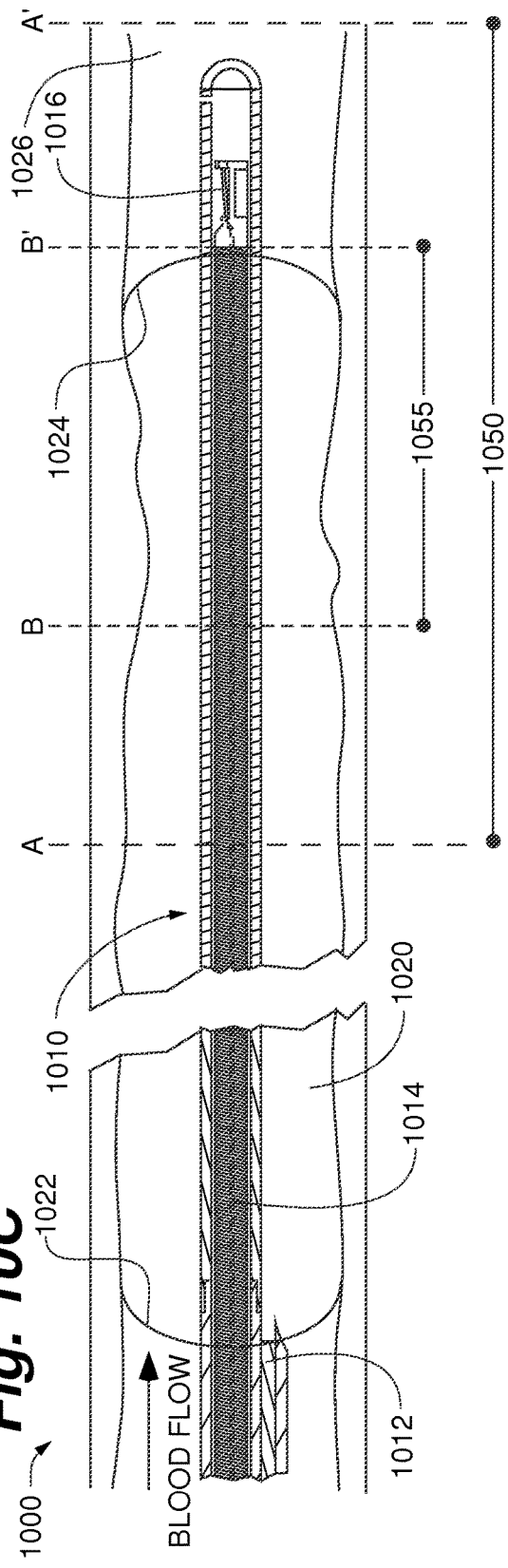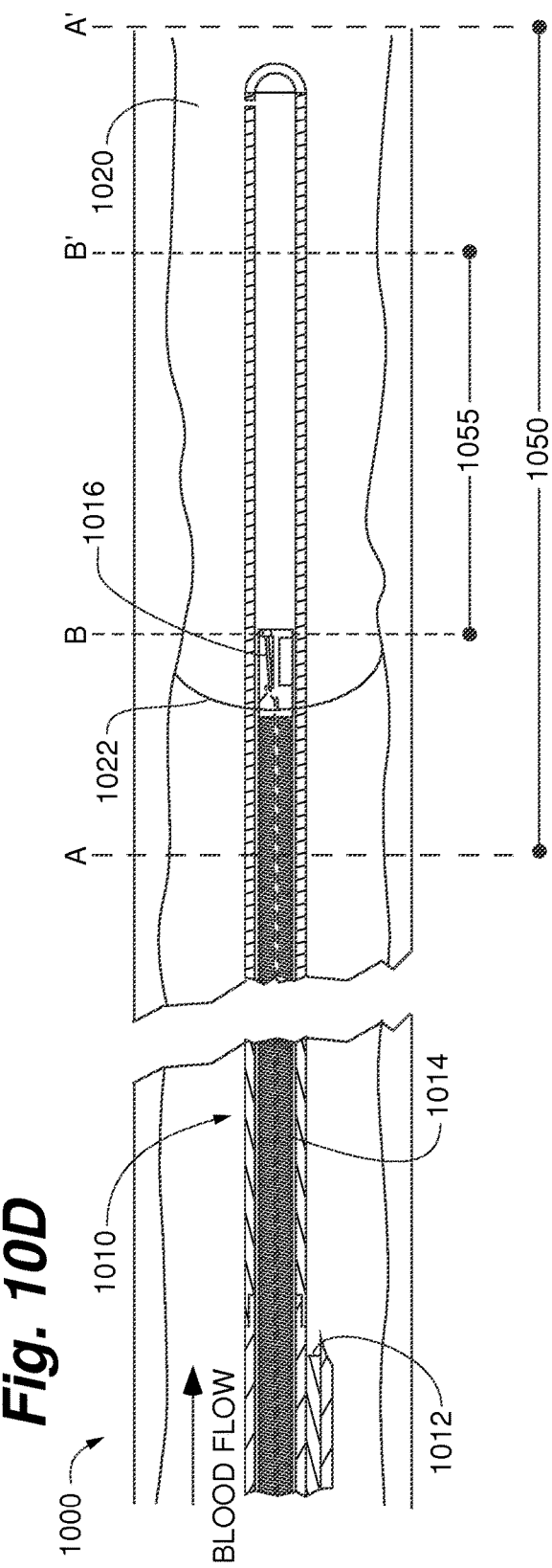

INTRAVASCULAR IMAGING

BACKGROUND

Intravascular imaging is often used to identify diagnostically significant characteristics of a vessel. For example, an intravascular imaging system may be used by a healthcare professional to help identify and locate blockages or lesions in a vessel. Common intravascular imaging systems include intravascular ultrasound (IVUS) systems as well as light-based imaging systems, such as infrared spectroscopy or optical coherence tomography (OCT) systems.

IVUS systems include one or more ultrasound transducers emitting ultrasound energy based on received electrical signals and sending return electrical signals based on ultrasound energy reflected by various intravascular structures. In some instances, a console with a high-resolution display is able to display IVUS images in real-time. In this way, IVUS can be used to provide in-vivo visualization of the vascular structures and lumens, including the coronary artery lumen, coronary artery wall morphology, and devices, such as stents, at or near the surface of the coronary artery wall. IVUS imaging may be used to visualize diseased vessels, including coronary artery disease. In some instances, the ultrasound transducer(s) can operate at a relatively high frequency (e.g., 10 MHz-60 MHz, in some preferred embodiments, 40 MHz-60 MHz) and can be carried near a distal end of an IVUS catheter. Some IVUS systems involve rotating the IVUS catheter (e.g., mechanically, phased-array, etc.) for 360-degree visualization.

With the advent of higher frequency IVUS imaging systems as well as light-based imaging systems, the precision of the image of the vessel is significantly improved when blood is displaced from the lumen of the vessel. Accordingly, imaging systems may include an injection system configured to deliver a flushing agent into the vessel before the vessel is imaged.

SUMMARY

This disclosure generally relates to systems and methods that may be used to generate blood-displaced intravascular images of areas of particular interest while minimizing the duration of blood displacement. In certain examples, an intravascular imaging system employing IVUS, light-based imaging, or other suitable imaging technique may be used to generate an intravascular image. In one example, the intravascular imaging system may be configured to assist a healthcare professional to identify diagnostically significant characteristics of a patient's vessel by generating a screening image of a section of the vessel, identifying one or more sub-sections within the section of the vessel containing a diagnostically significant characteristic of the vessel, and imaging the one or more sub-sections. The intravascular imaging system may be configured to perform one or more of these steps manually or automatically. For example, the intravascular imaging system may be configured to assist a user to manually identify one or more sub-sections, or the system may be configured to automatically identify the sub-sections based on the imaging data associated with the screening image. In another example, the intravascular imaging system may be configured to automatically image the one or more sub-sections after the sub-sections are identified. According to some examples, the intravascular imaging system may be configured to provide blood displacement to enhance image quality of the screening image and/or the image of the sub-section. In some examples, the intravascular imaging system may be configured to synchronize the imaging of a vessel with the blood displacement to minimize the period of time in which blood is displaced in the vessel.

Examples described in this disclosure may provide one or more advantages over existing systems and methods. For example, some of the described intravascular imaging systems and methods streamline the diagnostic process, thereby providing for time and cost savings to both the healthcare professional and a patient. In certain examples, diagnostically significant characteristics of a patient's vessel may be quickly identified, either manually or automatically, based on one screening image. Examples where diagnostically significant characteristics are automatically identified may provide for better healthcare for the patient as they may supplement the healthcare professional's diagnostic abilities. In situations where there are multiple diagnostically significant characteristics of a vessel that need to be imaged, some of the systems and methods can efficiently image the characteristics of the vessel, thereby minimizing patient discomfort. In certain examples involving blood displacement, described systems and methods can synchronize imaging with blood displacement to minimize negative consequences associated with blood displacement.

The details of one or more examples are set forth in the accompanying drawings and the description below. Other features, objects, and advantages will be apparent from the description and drawings, and from the claims.

BRIEF DESCRIPTION OF DRAWINGS

FIG. 3A is a side cross-sectional view of a catheter assembly.

FIG. 3B is a side cross-sectional view of a distal section of a catheter assembly.

FIG. 3C is a side cross-sectional view of a catheter assembly.

FIG. 4 is an illustrative example of a user interface of an imaging engine.

FIG. 7 is a flow diagram illustrating a method for generating a blood displaced image of a vessel.

FIG. 8B is a flow diagram illustrating a method for determining a volume of a quantity of fluid to displace blood.

FIGS. 10A-10D are cross-sectional views of a catheter assembly in a vessel.

DETAILED DESCRIPTION

The following detailed description is exemplary in nature and is not intended to limit the scope, applicability, or configuration of the invention in any way. Rather, the following description provides some practical illustrations for implementing examples of the present invention.

Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Figure 1:
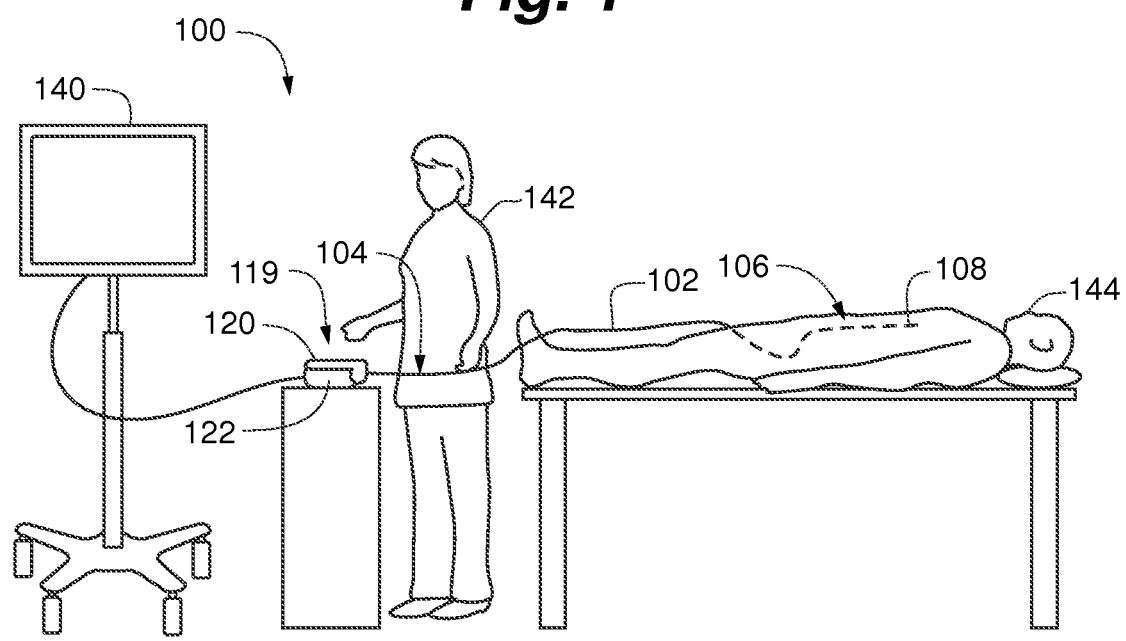
FIG. 1 is an illustrative example of a system configured to perform intravascular imaging.

FIG. 1 is an illustrative example of a system 100 that may be configured to perform intravascular imaging. System 100 may include a catheter assembly 102, a translation device 119, and an imaging engine 140. The catheter assembly 102 may include a proximal end 104 and a distal end 106 configured to be inserted into a vessel of a patient 144. In one example, catheter assembly 102 may be inserted into the patient 144 via the femoral artery and guided to an area of interest within the patient 144. The broken lines in FIG. 1 represent portions of catheter assembly 102 within the patient 144.

In some examples, catheter assembly 102 may include an intravascular imaging device 108 within distal end 106 configured to emit and receive wave-based energy and generate imaging data—e.g., to image the area of interest within the patient 144. For example, where system 100 is an IVUS system, intravascular imaging device 108 may comprise an IVUS imaging probe including an ultrasound transducer configured to emit and receive ultrasound energy and generate ultrasound data. In another example, system 100 may be an OCT system wherein the intravascular imaging device 108 may comprise an OCT imaging probe configured to emit and receive light and generate OCT data.

The translation device 119 may be configured to translate the intravascular imaging device 108 of the catheter assembly 102. The translation device 119 may comprise a linear translation system (LTS) 122. As is discussed elsewhere herein, LTS 122 may be mechanically engaged with catheter assembly 102 and configured to translate the catheter assembly 102 a controlled distance within the patient 144 during a translation operation, for example a pullback or push-forward operation. System 100 may comprise a patient interface module (PIM) 120 configured to interface the translation device 119 with the catheter assembly 102.

The imaging engine 140 may be in communication with the intravascular imaging device 108 and the translation device 119. According to some examples, the imaging engine 140 may comprise at least one programmable processor. In some examples, the imaging engine 140 may comprise a computing machine including one or more processors configured to receive commands from a system user 142 and/or display data acquired from catheter assembly 102 via a user interface. The computing machine may include computer peripherals (e.g., keyboard, mouse, electronic display) to receive inputs from the system user 142 and output system information and/or signals received from catheter assembly 102 (e.g., rendered images). In some examples, the user interface of the computing machine may be a touchscreen display configured to act as both an input device and an output device. In some examples, imaging engine 140 may include memory modules for storing instructions, or software, executable by the one or more processors.

The structure of imagine engine 140 can take a variety of forms. In some embodiments, the imaging engine can be made of an integrated machine that is configured to displace blood and to generate the screening and blood-displaced images. In some embodiments, the imaging engine can include separate injection and imaging apparatuses. In some such embodiments, the injection apparatus can be configured to displace blood, and the imaging apparatus can be configured to generate the screening and blood-displaced images. In some embodiments involving separate injection and imaging apparatuses, the two separate apparatuses can be configured to communicate and synchronize with one another. In some embodiments involving separate injection and imaging apparatuses, the injection apparatus can include a manual injection apparatus.

Figure 2:
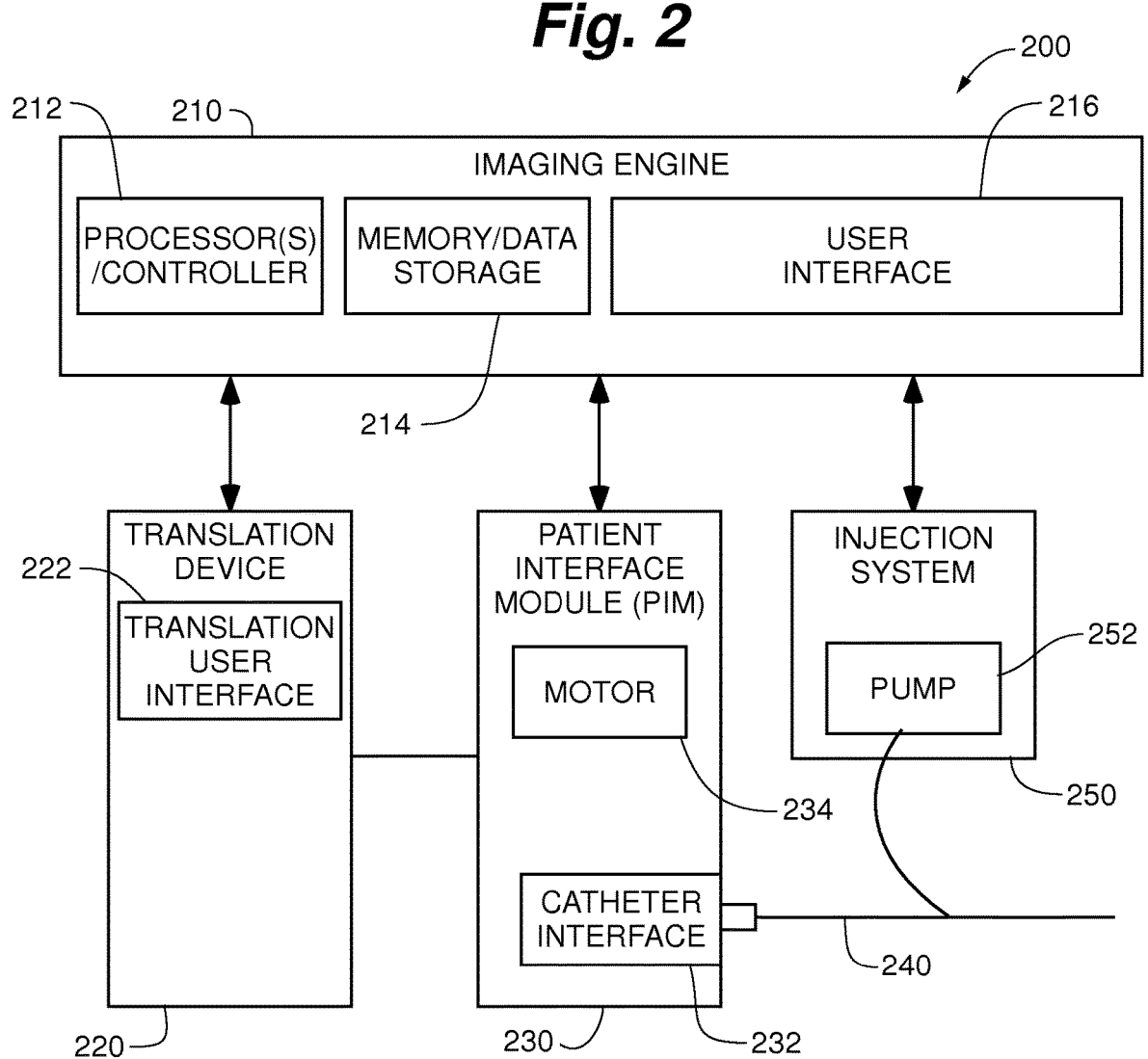
FIG. 2 is a block diagram illustrating a system configured to perform intravascular imaging.

FIG. 2 is a block diagram illustrating a system 200 configured to perform intravascular imaging. System 200 may include a PIM 230, a translation device 220, an injection system 250, a catheter assembly 240, and an imaging engine 210. System 200 may be configured to be used with an OCT and/or an IVUS based intravascular imaging device.

According to some examples, PIM 230 may provide an electromechanical interface between catheter assembly 240 and imaging engine 210. In some examples, PIM 230 may provide a catheter interface 232 to secure catheter assembly 240 to system 200. The PIM 230 may include a motor 234 configured to provide mechanical energy to rotate an intravascular imaging device of catheter assembly 240. According to some examples, PIM 230 may provide an electrical interface that transmits signals from the intravascular imaging device of catheter assembly 240 and receives return signals. In some examples, the intravascular imaging device may be electrically rotated via a phased array of ultrasound transducers.

Translation device 220 may be configured to provide longitudinal translation of the catheter assembly. Translation device 220 may comprise a Linear Translation System (LTS). The translation device 220 may be configured to mate with PIM 230 and catheter assembly 240 to enable controlled pullback of an intravascular imaging device of catheter assembly 240. According to some examples, translation device 220 may feature a translation user interface 222 which may comprise a translation display configured to display translation data associated with the translation of the intravascular imaging device to a user of system 200. In some examples, translation data may include linear distance traversed and/or translation speed. The translation user interface 222 may be configured to receive inputs from a user to control starting/stopping translation, setting translation speed, resetting linear distance traversed to zero, and/or switching to manual mode. In manual mode, a user may freely move the intravascular imaging device of the catheter assembly forward and backward (e.g., distally and proximally). In some examples, the translation device 220 may be configured to enable both pullback and push-forward of the intravascular imaging device at a controlled rate. In another example, the translation device 220 may be configured to oscillate, or cycle, the intravascular imaging device by alternately performing pullback and push-forward operations. In some examples, translation device 220 may include a position sensor configured to measure a distance of a translation operation.

Injection system 250 may be configured to deliver fluid into a vessel of a patient via the catheter assembly 240. Injection system 250 may comprise an injector pump 252 configured to deliver one or more fluids (e.g., contrast or saline) into the patient. In some examples, the injector pump 252 may be automated, in electrical communication with, and controlled by imaging engine 210. According to some examples, injector pump 252 may comprise a manual pump (e.g., syringe injection) configured to allow a user to manually deliver one or more fluids into the patient. As is discussed elsewhere herein, the injection system 250 may be in fluid communication with an intravascular blood displacement fluid port, which may be associated with catheter assembly 240, such that fluid from the injection system 250 is delivered into a patient's vasculature via the intravascular blood displacement fluid port. As can be appreciated, the injection system 250 may be configured to deliver any number of fluids and any quantity of fluid as appropriate for a specific application of system 200. In some examples, the quantity of blood displacement fluid may comprise a contrast media. In some examples, the quantity of blood displacement fluid may comprise saline.

FIG. 3A is a side cross-sectional view of a catheter assembly 300 that may be used in system 200 of FIG. 2. Referring again to FIG. 3A, a drive cable 304 of the catheter assembly 300 may be mechanically engaged and electrically connected to a PIM via a connector 302. Accordingly, the PIM may be used to rotate drive cable 304 within sheath 303. Intravascular imaging device 309 may be coupled to drive cable 304 such that rotation of the drive cable 304 causes an imaging element 308 to rotate in a distal section 330 of the catheter assembly 300. The imaging element 308 may be configured to emit and receive wave-based energy and generate imaging data. The imaging data may then be communicated to an imaging engine where the imaging data may be rendered into an image. In examples where catheter assembly 300 is configured for use in an IVUS system, imaging element 308 may comprise an ultrasound transducer. In examples where catheter assembly 300 is configured for use in an OCT system, imaging element 308 may comprise an OCT imaging probe configured to emit and receive light. In some examples, catheter assembly 300 may include an imaging window 306 substantially transparent to the frequency of the wave-based energy emitted by imaging element 308.

As noted, in some examples, an injection system may deliver a quantity of fluid (e.g., a bolus of fluid) through an intravascular blood displacement fluid port into a vessel of a patient. In some such examples, catheter assembly 300 may include an injection cannula 342 in fluid communication with the injection system upstream of point 340. The injection cannula 342 can include an injection cannula lumen 344 and an intravascular blood displacement fluid port 346 for delivering the fluid into the vessel. The injection system may deliver small boluses of fluid (e.g., saline or contrast dye) into the injection cannula lumen 344, out the intravascular blood displacement fluid port 346, and into the vessel. The blood displacement fluid port 346 may be located in a proximal section 320 of the catheter assembly 300 upstream of imaging element 308 such that the injected bolus will travel along with the blood flow within the vessel (i.e., left to right with reference to FIG. 3A) towards the imaging element 308. The bolus may comprise fluid that is substantially transparent to the wavelength of the wave-based energy emitted by imaging element 308 and used as a flushing agent to clear the vessel of blood to allow for enhanced imaging of the vessel.

FIG. 3B is a side cross-sectional view of a distal section 350 of a catheter assembly. In some examples, distal section 350 may be used in lieu of distal section 330 included in catheter assembly 300 of FIG. 3A. Distal section 350 can be similar to distal section 330 of catheter assembly 300 except that distal section 350 may include a monorail guidewire system 351. The monorail guidewire system 351 may include a distal end 352 forming a guidewire lumen 356 configured to accept a guidewire 354 to guide the catheter assembly into a vascular system of a patient. It can be appreciated that different examples may be configured to accept different guidewires depending on the application of the catheter assembly.

FIG. 3C is a side cross-sectional view of a catheter assembly 370 that may be used in system 200 of FIG. 2. Referring again to FIG. 3C, in some examples, catheter assembly 370 may include a guide catheter 380 configured to deliver an intravascular imaging device 390 to an area of interest within a patient. Intravascular imaging device 390 may be coupled to a drive cable 394 such that rotation of the drive cable 394 causes an imaging element 399 to rotate in a distal section 395 of the catheter assembly 370. According to some examples, intravascular imaging device 390 may be substantially enclosed by sheath 385. In some examples, catheter assembly 370 may be in fluid communication with an injection system to deliver a quantity of fluid from the injection system to a vessel of a patient. In such examples, guide catheter 380 may deliver the quantity of fluid from the injection system to the vessel via a space 382 between guide catheter 380 and sheath 385. Fluid delivered by guide catheter 380 may enter the vessel at an intravascular blood displacement fluid port 384.

Referring back to FIG. 2, imaging engine 210 of system 200 may comprise one or more processors 212, one or more memory modules 214, and a user interface 216. Imaging engine 210 may be configured to perform one or more functions including, for example, image generation, display of intravascular images and other information, control of the system components, storing and exporting the image data, controlling user interface 216 for operating the system 200, analysis tools (e.g., area measurements, linear measurements, and annotations), hemodynamic calculations, and so on.

The one or more memory modules 214 may include instructions that may be executed by the one or more processors 212 (e.g., software). The memory modules 214 may comprise one or more non-transitory computer readable storage media which may include volatile and/or non-volatile memory forms including, e.g., random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media. In some examples, instructions may be embedded or encoded in the memory modules 214 which may cause the one or more processors 212 to perform a method, e.g., when the instructions are executed.

In some examples, user interface 216 may be configured to receive inputs from a user of system 200 and may comprise one or more computer peripherals (e.g., keyboard, mouse), voice recognition technology, or other suitable means of receiving inputs from a user. User interface 216 may include a display configured to display imaging data (e.g., intravascular images, system status, hemodynamic measurements) to a user of system 200. In some examples, the user interface 216 may comprise a touch-sensitive screen configured to receive user inputs as well as display imaging data.

FIG. 4 is an illustrative example of a user interface 400 of an imaging engine that may be used in system 200 of FIG. 2. User interface 400 may comprise a menu 410, a data display area 420, and an image display area 430. Menu 410 may be configured to receive inputs from a user and may include graphical icons configured to perform specific functions or tasks when selected. In some examples, a user may interact with the menu 410 by using a computer peripheral (e.g., mouse, keyboard) to select the graphical icons. In examples where user interface 400 comprises a touch screen, a user may simply touch the graphical icons displayed by user interface 400. Data display area 420 may be used to display imaging data or other relevant data to the user. Image display area 430 may be used to display intravascular images generated by an imaging engine to the user, for example a cross-sectional view of a vessel of a patient. In some examples, image area 420 may display a screening image of a section of the patient's blood vessel. FIG. 4 is provided only for the purposes of illustration and not limitation. One skilled in the art will appreciate that there are a multitude of configurations for user interface 400 within the scope and spirit of the invention.

According to some examples, an imaging engine may be configured to generate a screening image of a section of a patient's blood vessel and identify a sub-section of the patient's blood vessel within the section for further imaging. In many instances, the screening image can be generated (510) without displacement of blood or with only partial displacement of blood. In such instances, the section imaged in the screening image generation step (510) can be significantly larger than the sub-section that will be the subject of further imaging. Imaging the comparatively large section without blood displacement (or with only partial blood displacement) and then imaging only the comparatively small sub-section with a greater degree of blood displacement (up to full blood displacement) can result in a smaller quantity and shorter duration of blood displacement. In many examples, the sub-section of the patient's blood vessel is less than all of the section of the patient's blood vessel (though in some instances the entire section may warrant further imaging).

Figure 5A:
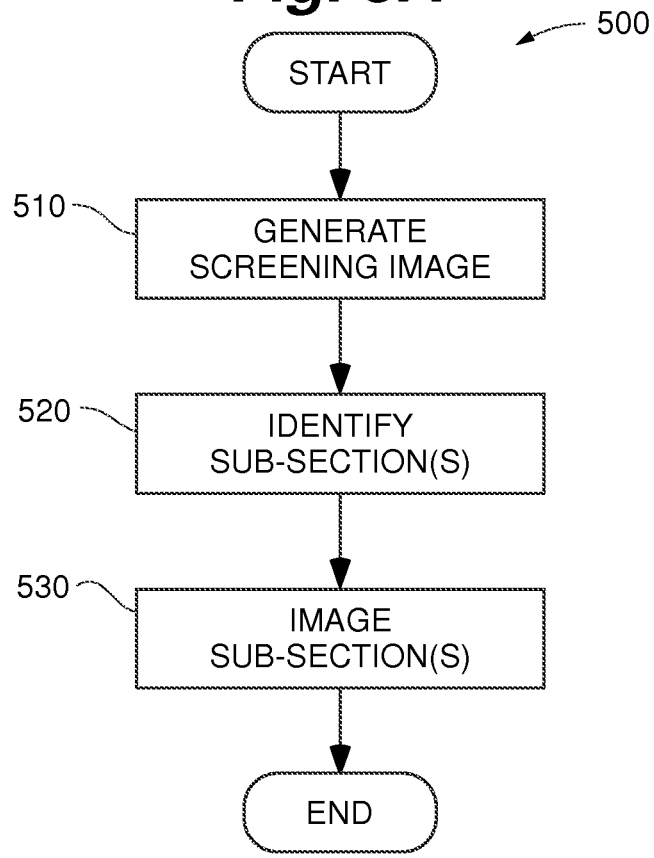
FIG. 5A is a flow diagram illustrating a method for imaging a vessel.
Figure 5B:
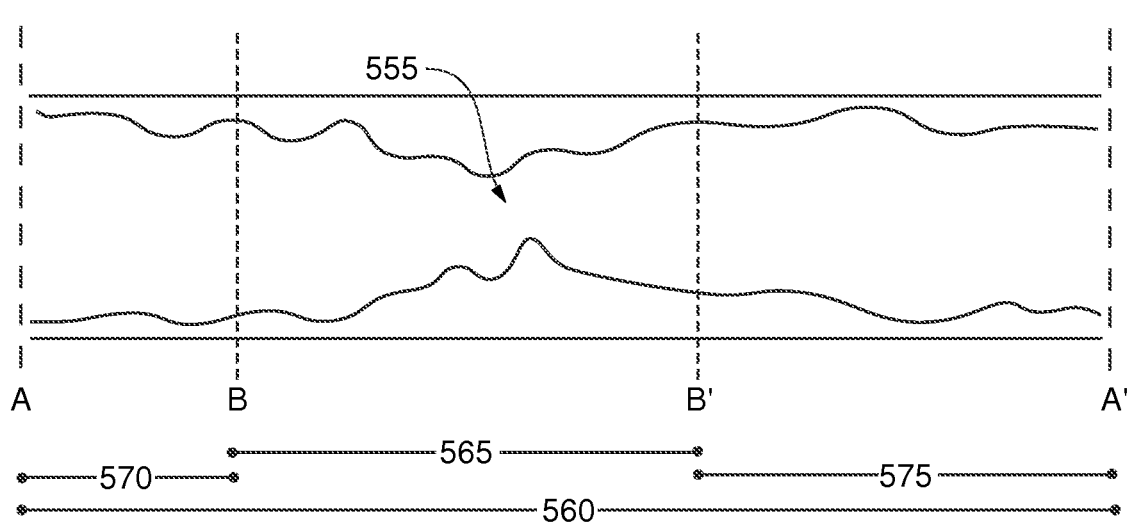
FIG. 5B shows a cross-sectional view of a vessel.

FIG. 5A is a flow diagram illustrating a method 500 for imaging a vessel, and FIG. 5B shows a cross-sectional view of a vessel 550 that may be imaged according to the method 500 of FIG. 5A. With reference to FIGS. 5A and 5B, an imaging engine may be configured to generate a screening image (510) of a vessel 550 of a patient. In this example, the screening image comprises a section 560 between points A and A' and may be generated based on imaging data collected by an intravascular imaging device. In some examples, a user may manually generate a screening image (510) by directing an imaging engine to image between points A and A'. In other examples, an imaging engine may automatically generate a screening image (510) by determining points A and A' and imaging between points A and A'.

Referring to FIG. 5A, the imaging engine may then identify a sub-section (520) of the section that warrants further imaging. In FIG. 5B, the sub-section 565 is between points B and B' within section 560. In some examples, sub-section 565 may be identified based on imaging data representative of diagnostically significant characteristics of the vessel 550 (e.g., blockages, lesions, location of stent, etc.). For example, sub-section 565 may be identified based on imaging data indicative of a narrowing portion 555 of the vessel 550. In some examples, the imaging engine may be configured to allow a user to manually identify and select sub-section 565 by interacting with a user interface of the imaging engine. In such examples, the user may identify by visually examining the screening image and selecting one or more sub-sections relative to, or on, the screening image (e.g., clicking and dragging a section of the screening image using a mouse or finger, etc.). In some examples, the imaging engine may be configured to automatically identify 520 one or more sub-sections by analyzing the screening image and/or the imaging data associated with the screening image to recognize diagnostically significant characteristics of the vessel. For example, the imaging engine can compare data acquired from various positions along the section (e.g., dimensional data, such as lumen cross-sectional area) and determine which sub-section(s) warrant further imaging.

Figure 6:
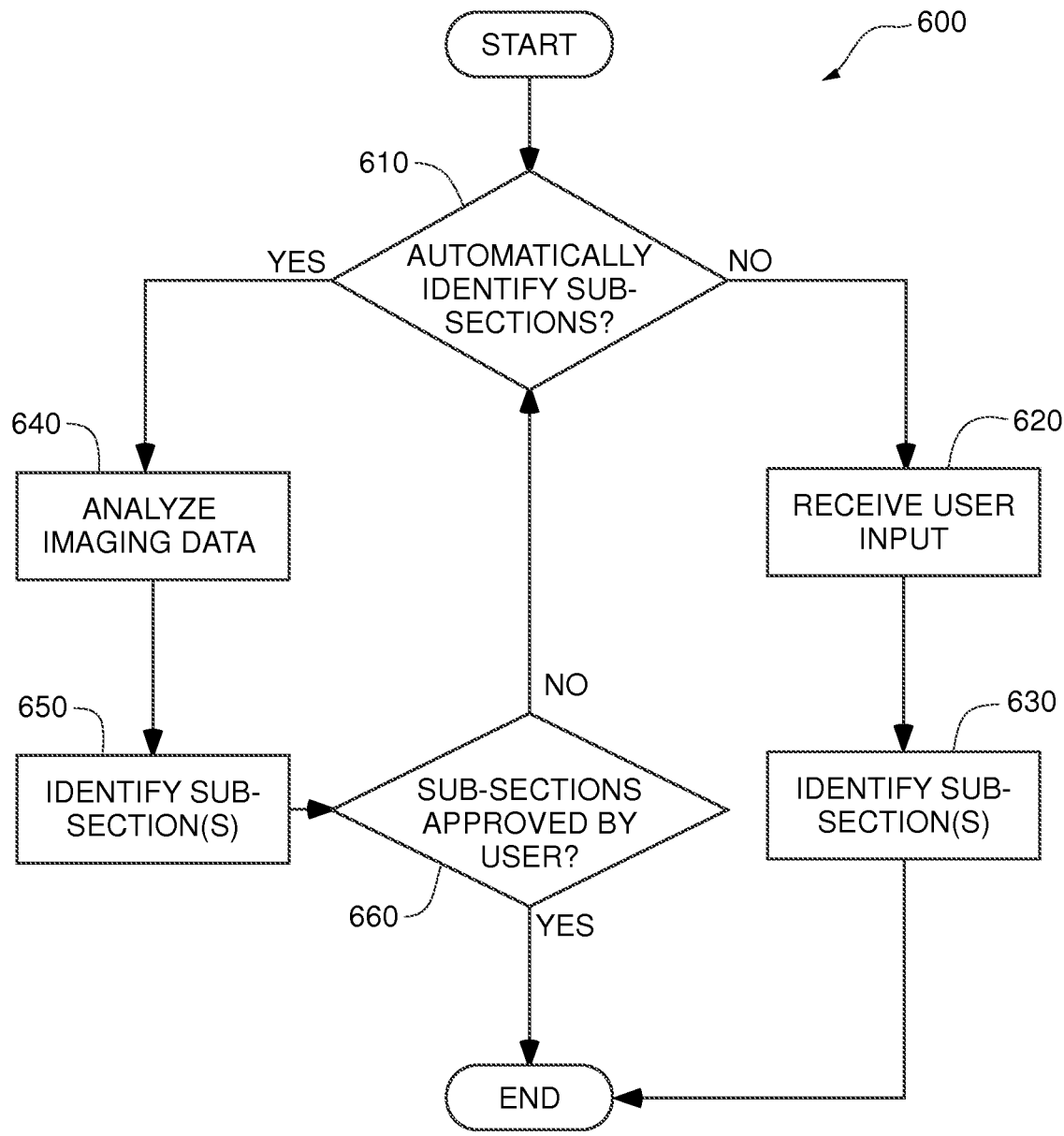
FIG. 6 is a flow diagram illustrating a method for identifying a sub-section within a section of a vessel.

According to some examples, an imaging engine may be configured to provide a user the option of manual or automatic identification of one or more sub-sections. FIG. 6 is a flow diagram illustrating a method 600 for identifying a sub-section within a section of a patient's blood vessel. Method 600 provides a user the option to choose whether one or more sub-sections are to be identified automatically or manually for further imaging. According to some examples, step 520 of FIG. 5A may comprise the steps of method 600 of FIG. 6. After an imaging engine has collected imaging data and generated a screening image of a section of patient's blood vessel, the imaging engine may prompt a user in step (610) to indicate whether the user would like to manually identify sub-sections for further imaging or have the imaging engine automatically identify sub-sections. If the user chooses to manually identify sub-sections, the imaging engine then receives (620) user input indicative of a sub-section. As noted, a user may manually identify a sub-section via a user interface of the imaging engine, for example user interface 400 of FIG. 4. Referring again to FIG. 6, after receiving user input (620), the imaging engine may then identify the one or more sub-sections (630) before continuing to image the manually selected sub-sections. If the user chooses in step (610) to have the imaging engine automatically identify sub-sections, the imaging engine then analyzes the imaging data (640) and/or the associated screening image for potential diagnostically significant characteristics found within the section of the vessel. The imaging engine may then identify one or more sub-sections (650) for further imaging. In some examples, the imaging engine may prompt the user to approve the automatically identified sub-sections (660). In some examples, the imaging engine may be configured to present to the user the screening image where the one or more sub-sections, or the potential diagnostically significant characteristics, are made distinct (e.g., magnified, highlighted) on the screening image. In such examples, a user interface of the imaging engine may be used to present data and receive inputs from the user. As can be appreciated, step (660) may reduce improperly identified sub-sections of the vessel that may not contain diagnostically significant or relevant characteristics of the vessel. In many examples, a user approval step (660) is omitted. In some such examples, a user can choose automatic selection of the sub-section and simply receive an enhanced image of the sub-section without providing further input.

Where the imaging engine identifies more than one sub-section in step (650), a user may approve all, none, or a subset of the automatically identified sub-sections. If a user rejects an automatically identified sub-section, the imaging engine may again prompt the user in step (610) to indicate whether the user would like to manually or automatically identify sub-sections. In situations where a user approves a subset of automatically identified sub-sections, the imaging engine may be configured to store the approved sub-sections to avoid redundant identification of sub-sections as steps of method 600 are repeated. In some examples, an additional step may be employed between steps 610 and 640 wherein a user is given the option to enter criteria to assist an imaging engine to identify relevant sub-sections. For example, a user only interested in imaging blockages in the patient's vessel may direct the imaging engine to only automatically identify sub-sections including blockages and exclude all other diagnostically significant characteristics of the vessel. In another example, a user only interested in imaging stented areas may direct the imaging engine to only automatically identify sub-sections including stents and exclude all other diagnostically significant characteristics of the vessel.

In situations involving more than one sub-section to be imaged, the imaging engine may be configured to determine an optimized order of imaging for the sub-sections. Optimization may be based on the position of the sub-sections within the vessel, the current position of the imaging element and/or catheter assembly, or other relevant factors. In some examples, the imaging may provide a suggested order of imaging to the user and allow the user to approve or edit the order via a user interface.

Referring back to FIG. 5A, once sub-section is identified (520), the imaging engine may then image the sub-section (530). Again, in FIG. 5B, the sub-section 565 is between points B and B' within section 560. Referring again to FIG. 5A, in some examples, imaging the sub-section (530) may be initiated manually by a user via a user interface of an imaging engine. In other examples, an imaging engine may be configured to automatically image the sub-section (530). In such examples, an imaging engine may be configured to automatically translate an intravascular imaging device through the sub-section with a translation device to image the sub-section (530) of a vessel based on the identification of the sub-section (520). For example, an imaging engine may generate a screening image of vessel (510) by directing a translation device to perform a pull-back operation from point A' to point A. The imaging engine may then determine a physical distance of section 560 based on the mechanical positions of the translation device at points A and A' in FIG. 5B. After sub-section 565 is identified, the imaging engine may then determine a physical distance of sub-section 565. In some examples, this determination may be based on a ratio between the lengths of sub-section 565 and section 560 (i.e., the ratio of the distance between B and B' and the distance between A and A'), and the known physical distance of section 560. In some examples, the ratio between the sub-section 565 and section 560 need not be physical distances; rather, they can be any representation of the lengths sufficient to determine a ratio, for example a number of pixels representative of the respective lengths. In some examples, the physical distances of portions 570 and 575 may be determined using a similar method. The imaging engine may then automatically position the intravascular imaging device at either point B or B' based on the physical distances of sub-sections 565, 570, and/or 575 to image sub-section 565. An imaging engine may be configured to automatically image 530 multiple sub-sections in succession based on one or more screening images.

Referring again to FIG. 5A, according to some examples, an imaging engine may be configured to automatically displace blood while imaging one or more sub-sections of a patient's vessel (530). Generally, the presence of blood during intravascular imaging affects the quality of the images. For example, blood may be a cause of speckle in images captured using IVUS imaging systems as the content of blood (e.g., red blood cells, white blood cells, platelets) is too small to be resolved by an ultrasound transducer. Generally, speckle is considered an undesirable image artifact as it can mask potentially diagnostically significant imaging features. In OCT imaging systems, wherein images are generated based on the emission and receiving of light, blood in a vessel may significantly inhibit the ability to generate an intravascular image. Thus, blood displacement methods and techniques are often used in connection with intravascular imaging to enhance image quality. Accordingly, some examples include an imaging engine configured to generate a screening image with minimal blood displacement and then generate an enhanced image of a sub-section of interest with a greater degree of blood displacement. The enhanced image can involve the imaging engine displacing blood within the patient's blood vessel by introducing a quantity of blood displacement fluid into the patient's blood vessel via an intravascular blood displacement fluid port, and generating a blood-displaced image of the sub-section while blood within the sub-section is displaced by the quantity of blood displacement fluid. The blood displacement fluid may comprise a flushing agent substantially transparent to the wavelength used by an imaging element to collect imaging data (e.g., saline, contrast, Ringer's solution, dextran, lactate solution, etc.).

FIG. 7 is a flow diagram illustrating a method 700 for generating a blood-displaced image of a vessel of a patient. According to some examples, step (530) of FIG. 5A may comprise the steps of method 700 of FIG. 7. After one or more sub-sections have been identified, an imaging engine may automatically position an intravascular imaging device (710) to translate the intravascular imaging device through the sub-section with a translation device. In some examples, positioning the intravascular imaging device (710) may comprise aligning an imaging element of the intravascular imaging device with a distal or proximal end of the sub-section to be imaged such that the imaging engine may perform an appropriate translation operation to scan the sub-section. Once the intravascular imaging device has been placed in position to image the sub-section, the imaging engine may start blood displacement (720) in the vessel. In some examples, the imaging engine may direct an injection system to introduce a quantity of fluid into the vessel of the patient via an intravascular blood displacement fluid port. The imaging engine may automatically image the sub-section (730) once blood has been displaced from the sub-section. In some examples, the imaging engine may direct a translation device to translate the intravascular imaging device through the sub-section (e.g., pullback and/or push-forward operations). At the same time, an imaging element of the intravascular imaging device can collect imaging data. Once the area of interest has been imaged (730), the imaging engine may stop blood displacement (740).

In some embodiments, when a screening image of a section of a patient's blood vessel has been generated and when a sub-section within the section has been identified, the imaging engine may initiate multiple additional steps automatically. For example, the imaging engine can automatically displace blood within the patient's blood vessel by introducing a quantity of blood displacement fluid into the patient's blood vessel. The imaging engine can automatically translate an intravascular imaging device through the sub-section with a translation device. The imaging engine can automatically generate a blood-displaced image of the sub-section while blood within the sub-section is displaced by the quantity of blood displacement fluid and while the intravascular imaging device is translating through the sub-section. In some such embodiments, after the sub-section of interest has been identified (either manually or automatically), the imaging engine can automatically take all necessary steps to generate a blood-displaced image of the sub-section without further user input.

Despite the benefits provided by blood displacement to intravascular imaging, in many instances it may be beneficial to minimize the amount of time blood is displaced from a vessel. Prolonged periods of blood displacement may cause anoxic episodes, which may stress tissue downstream of an area of interest of the vessel. In some examples the imaging engine may be configured to start and stop displacing blood from the sub-section of the patient's blood vessel based on a position of the translation device. For example, as the translation device translates the intravascular imaging device, the position of the translation device may be indicative as to when an intravascular imaging device is in position to begin imaging the sub-section and when imaging of the sub-section is complete. In this way, blood can be displaced for a minimum amount of time to image the sub-section.

In examples utilizing IVUS imaging, to minimize prolonged periods of blood displacement, a screening image may be generated without displacing blood. Despite the presence of image artifacts caused by imaging a vessel filled with blood (e.g., speckle), certain diagnostically significant characteristics of the vessel may be identified nevertheless. In some examples, where identification of the diagnostically significant characteristics of the vessel may be inhibited, a user may opt to generate a blood-displaced screening image. In examples utilizing OCT imaging, an at least partially blood-displaced screening image may be necessary due to the opacity of blood. In examples utilizing both IVUS and light-based imaging, a non-blood displaced screening image may be generated by IVUS and a blood-displaced image of sub-sections may be generated by IVUS and/or light-based imaging.

Figure 8A:
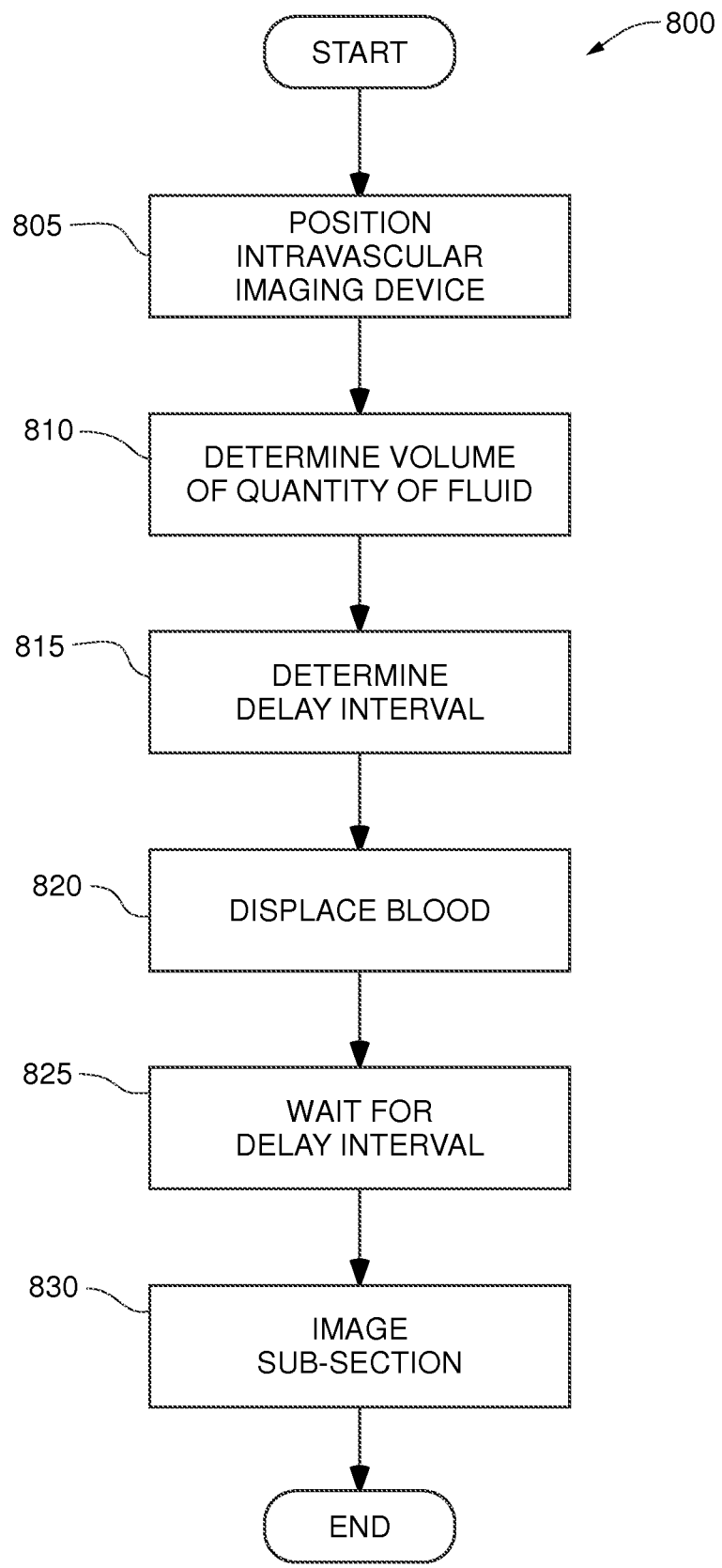
FIG. 8A is a flow diagram illustrating a method for generating a blood displaced imaging of a blood vessel.

To minimize prolonged periods of blood displacement, an imaging engine may be configured to be in communication with, and/or synchronized to, an injection system. Accordingly, in some examples the imaging engine may be configured to start displacing blood from the sub-section of the patient's blood vessel at substantially the same time as when the imaging engine starts generating the blood-displaced image of the sub-section. Similarly, an imaging engine may be configured to stop displacing blood from the sub-section of the patient's blood vessel at substantially the same time as when the imaging engine stops generating the blood-displaced image of the sub-section. FIG. 8A is a flow diagram illustrating a method 800 for generating a blood displaced image of a vessel of a patient. According to some examples, step 530 of FIG. 5A may comprise the steps of method 800 of FIG. 8A. After one or more sub-sections have been identified, an imaging engine may position, using a translation device, an intravascular imaging device (805) to translate the intravascular imaging device through the sub-section(s). Once the intravascular imaging device is in position to image, the imaging engine may determine a volume of a quantity of fluid (810) to be used to displace blood in the sub-section. To minimize the amount of time blood is displaced in a patient's vessel, an imaging engine may be configured to determine only the volume required to displace blood from the sub-section for the time it takes to image the sub-section. Once a volume of the quantity of fluid is determined, the imaging engine may be configured to determine a delay interval (815) to synchronize the imaging of the sub-section with the displacement of blood in the sub-section. In some examples, the delay interval may be the time it takes for a bolus of fluid (e.g., the volume of the quantity of fluid), to displace the blood from the sub-section after it is introduced into the vessel from an intravascular blood displacement fluid port. After the delay interval is determined (815), the imaging engine may then displace blood 820 from the vessel and wait (825) for the delay interval. Once the delay interval expires, the bolus of fluid will have displaced blood from the sub-section and the imaging engine may then image the sub-section (830).

In some examples, the imaging engine may be configured to determine a required volume of the quantity of blood displacement fluid based on a physical dimension of the sub-section of the patient's blood vessel as well as a longitudinal dimension, or length, of the sub-section to be imaged. FIG. 8B is a flow diagram illustrating a method 850 for determining a volume of a quantity of fluid to displace blood in a sub-section. According to some examples, step (810) of FIG. 8A may comprise the steps of method 850. The imaging engine may be configured to determine a physical dimension of a vessel (855). In some examples, the physical dimension may be a cross-sectional area of the sub-section to be imaged. Commonly owned U.S. patent application Ser. No. 13/834,031 ("Multiple Transducer Delivery Device and Method"), filed on Mar. 15, 2013, discusses, among other things, gathering information regarding the diameter or cross-sectional area of a blood vessel and is hereby incorporated by reference herein in its entirety. In some examples, the imaging engine may be configured to use the imaging data acquired in connection with the screening image to determine an average cross-sectional area of the sub-section to be imaged. After a physical dimension of the vessel is determined (855), the imaging engine may then determine a flow rate (860) of the vessel and/or the sub-section based on the physical dimension. Commonly owned U.S. patent application Ser. No. 13/902,224 ("Fluid Flow Measurement Systems and Methods"), filed on May 24, 2013, discusses, among other things, performing hemodynamic measurements including blood velocity and volumetric flow within a vessel and is hereby incorporated by reference herein in its entirety.

Once a flow rate has been determined (860), the imaging engine may then determine a longitudinal dimension, or length, of the sub-section (875) to be imaged. As noted, the longitudinal dimension of a sub-section to be imaged may be determined based on a known physical length of a screening image (e.g., measured by a position sensor of a translation device or derived using known mechanical positions of a translation device acquired while generating the screening image) and a ratio between the length of the sub-section and the section of the screening image (e.g., ratio of pixels of sub-section and section). Using the longitudinal dimension of the sub-section, the imaging engine may determine the time to image the sub-section (880) based on a known translation rate of the translation device. The imaging engine may then determine the volume of quantity of fluid (885) necessary to displace blood from the sub-section during imaging based on the flow rate determined in step (860) and the time to image the subsection determined in step (880). In some examples, the physical dimension, or a volume, of the sub-section of the patient's blood vessel may be determined based on a cross-sectional area of the sub-section and/or a length of the sub-section. In some examples, the imaging engine may take into account the volume or length of the sub-section to be imaged as well as known or calculated margins of error when determining the volume of the quantity of fluid (885) to displace blood from the sub-section.

Referring back to FIG. 8A, an imaging engine may determine a delay interval (815) (e.g., the time it takes to displace blood from the sub-section to be imaged) based on a determined flow rate within the vessel and a known distance between an imaging element and an intravascular blood displacement fluid port. As noted, the flow rate may be determined using methods disclosed in commonly owned U.S. patent application Ser. No. 13/902,224, previously incorporated by reference in its entirety, to perform hemodynamic measurements including blood velocity and volumetric flow within a vessel. The distance between the imaging element and the intravascular blood displacement fluid port may be known or derived based on one or more mechanical positions of a translation device, a position sensor of a translation device, and/or known lengths of the catheter assembly, intravascular imaging device and drive cable. Accordingly, an imaging element may be configured to determine the delay interval (815) based on the determined flow rate and the known distance (e.g., divide the known distance by blood velocity).

Figure 9:
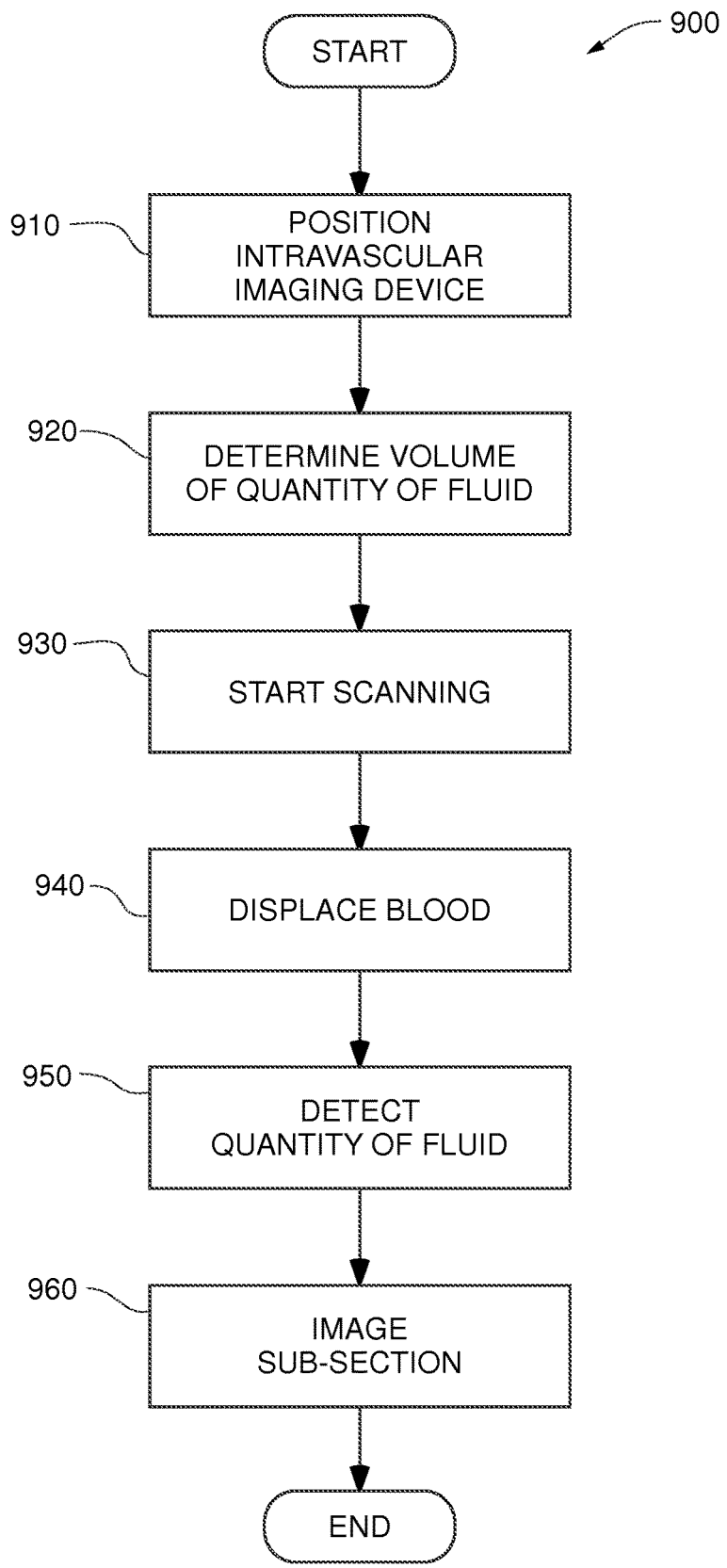
FIG. 9 is a flow diagram illustrating a method for generating a blood displaced image of a vessel.

In some examples, the imaging engine may be configured to detect when blood is displaced from the sub-section of the patient's blood vessel and generate the image of the sub-section after the detection of blood displacement from the sub-section. FIG. 9 is a flow diagram illustrating a method 900 for generating a blood displaced image of a vessel of a patient. According to some examples, step (530) of FIG. 5A may comprise the steps of method 900 of FIG. 9. Method 900 is similar to method 800 of FIG. 8A except method 900 begins imaging the sub-section (960) when a quantity of fluid is detected (950) instead of utilizing a delay interval as in method 800. Referring to FIG. 9, an imaging engine may position an intravascular imaging device (910) to translate the intravascular imaging device through a sub-section. The imaging engine may then determine an appropriate volume of a quantity of fluid (920). In some examples, step (920) may be similar to step (810) to determine a volume of a quantity of fluid as discussed with reference to FIG. 8A. Referring again to FIG. 9, the imaging engine may then direct the intravascular imaging device to start scanning (930) the vessel in the longitudinal position of step (910). Scanning the vessel (930) may comprise maintaining a stationary longitudinal position relative to the vessel, rotating the imaging element, and generating imaging data by emitting and receiving wave-based energy from the imaging element. While the intravascular imaging device is scanning the vessel (930), the imaging engine may displace blood (940) with the volume of the quantity of fluid determined in step (920). The imaging engine may then detect the quantity of fluid (950) in the vessel when the bolus reaches the scanning intravascular imaging device. Detection of the bolus indicates that the bolus of the quantity of fluid has displaced blood from the sub-section and the imaging engine may then image the sub-section (960) by performing a translation operation while the intravascular imaging device continues scanning.

According to some examples, an imaging engine may be configured to detect the position of a bolus comprising a flushing agent by scanning for the presence or absence of image artifacts associated with blood. For example, as noted, blood may cause an IVUS imaging system to generate an image artifact known as speckle because the content of blood (e.g., red blood cells, white blood cells, platelets) may be too small to be resolved by an ultrasound transducer. In contrast, flushing agents may not cause speckle as they are substantially transparent to the wave-based energy used for imaging. Accordingly, a density of speckle (e.g., the density of specks in an ultrasound image) may be directly correlated with a concentration of blood in a vessel and may be used to detect a bolus comprising a flushing agent in a vessel. In some examples the imaging engine may be configured to perform methods disclosed in commonly owned U.S. patent application Ser. No. 13/902,224, previously incorporated by reference in its entirety, to detect a bolus of fluid comprising a flushing agent using an intravascular imaging device.

In some examples, where the imaging engine is configured to generate a speckle density, a leading edge of the bolus of fluid comprising a flushing agent may be detected when the speckle density goes from high (e.g., speckle caused by blood) to low (e.g., absence of speckle in the flushing agent). Similarly, a trailing edge of the bolus may be detected when the speckle density goes from low (e.g., flushing agent) to high (e.g., blood). In some examples, one or more speckle density thresholds may be used to characterize the leading and/or the trailing edges of the bolus. In some examples, the speckle density threshold may be predetermined and/or selected by a user. In other examples, the measurement engine may be configured to automatically determine a speckle density based on a configuration of the system and/or the specific imaging conditions of the application.

Similar methods may be used to determine the position of a bolus using imaging technologies other than IVUS. As just one example, the methods described herein may be adapted for an imaging engine using OCT. For example, the bolus may comprise an optically transparent flushing agent and instead of detecting a speckle density, the OCT imaging engine may detect optical transparency or opacity of the fluid in the vessel to determine the position of the bolus. Accordingly, in some examples, optical transparency or opacity thresholds may be used to detect the position of the bolus.

FIGS. 10A-10D are cross-sectional views of a catheter assembly 1010 in a vessel 1000 of a patient. In this example, catheter assembly 1010 may include an intravascular blood displacement fluid port 1012 and an intravascular imaging device 1014 including an imaging element 1016. Catheter assembly 1010 may be configured to deliver a bolus 1020 of fluid into vessel 1000 via the intravascular blood displacement fluid port 1012. The bolus 1020 of fluid may be a quantity of fluid comprising a flushing agent. The sequence of FIGS. 10A-10D chronologically illustrates a method for imaging a sub-section 1055. For example, the sequence of FIGS. 10A-10D may be illustrative of the method 700 of FIG. 7, method 800 of FIG. 8A, or method 900 of FIG. 9.

Prior to FIG. 10A, an imaging engine may have already generated a screening image of a section 1050 of vessel 1000 between points A and A'. In FIG. 10A, the imaging engine has positioned imaging element 1016 to image sub-section 1055. More specifically, imaging element 1016 is positioned distal to point B' such that sub-section 1055 may be imaged via a pullback operation from point B' to point B. In other examples, the imaging engine may position imaging element 1016 proximal to point B such that sub-section 1055 may be imaged via a push-forward operation from point B to point B'. As shown in FIG. 10A, a bolus 1020 of fluid comprising a flushing agent is being released from intravascular blood displacement fluid port 1012.

FIG. 10B shows bolus 1020 getting larger as the imaging engine continues to inject the flushing agent into the vessel 1000 via the intravascular blood displacement fluid port 1012. As noted, in some examples the imaging element 1016 may determine and dispense only the volume of fluid necessary for the sub-section 1055 to be imaged to minimize prolonged blood displacement. As shown in FIG. 10B, the bolus 1020 is just about to displace the blood in sub-section 1055 as a leading edge 1024 of the bolus 1020 nears point B, the proximal end of sub-section 1055.

As shown in FIG. 10C, the leading edge 1024 of the bolus 1020 nears point B' thereby displacing the blood in sub-section 1055. Once blood is displaced in sub-section 1055, the imaging engine may begin to image sub-section 1055 via a pullback operation. In some examples, the imaging engine may commence imaging of sub-section 1055 based on a delay interval associated with the time it takes the leading edge 1024 of bolus 1020 to travel from the intravascular blood displacement fluid port 1012 to point B' (e.g., the time difference between FIGS. 10A and 10C). In some examples, the delay interval may be determined using a method similar to step 815 of FIG. 8A, as described herein. In other examples, the imaging engine may commence imaging of sub-section 1055 based on a detection of the leading edge 1024 of the bolus 1020. As described with reference to method 900 of FIG. 9, the imaging engine may begin scanning vessel 1000 generating imaging data via imaging element 1016 at point B'. Before the leading edge 1024 of bolus 1020 reaches point B', any imaging data generated by imaging element 1016 is with blood in vessel 1000. Once the leading edge 1024 reaches point B', the imaging data generated by imaging element 1016 is with the flushing agent of bolus 1020 in vessel 1000. In examples utilizing IVUS, the leading edge 1024 of bolus 1020 may be detected based on a decrease in speckle density from the speckle density of blood (high) to the speckle density of the flushing agent of bolus 1020 (low). In examples utilizing OCT, the leading edge 1024 of bolus 1020 may be detected based on a decrease in fluid opacity from the opacity of blood (high) to the opacity of the flushing agent of bolus 1020 (low). Once the leading edge 1024 is detected at point B', bolus 1020 has displaced the blood from sub-section 1055 and the imaging engine may commence imaging the sub-section 1055.

In some examples, the imaging element 1016 may be positioned at point B as the bolus 1020 moves from intravascular blood displacement fluid port 1012 toward the sub-section 1055. When the leading edge 1024 of the bolus 1020 reaches point B, the imaging engine may commence imaging of sub-section 1055. The imaging element 1016 may be pushed forward at a rate that correlates to the rate of the bolus 1020 moving through the vessel 1000. In this way, the imaging element 1016 and bolus 1020 travel through the sub-section 1055 together, with the imaging element 1016 gathering blood-displaced imaging data as it travels. In some such examples, the bolus 1020 can be only large enough to encompass the imaging element 1016. In some examples, the bolus 1020 need not be large enough to encompass the whole sub-section 1055. Many such examples result in minimal blood displacement.

In FIG. 10D, the imaging engine has completed imaging of sub-section 1055 as imaging element 1016 has reached the proximal end of sub-section 1055 at point B. FIG. 10D illustrates an example where the volume of bolus 1020 minimizes prolonged periods of blood displacement as a trailing edge 1022 of bolus 1020 nears point B just as imaging of sub-section 1055 is complete. Thus, blood is displaced for no longer than necessary for sub-section 1055 to be imaged.

The techniques and methods described in this disclosure may be embodied or encoded in a computer-readable medium, such as a non-transitory computer-readable storage medium containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), a hard disk, optical media, or other computer readable media.

Various examples have been described. These and other examples are within the scope of the following claims.

What is claimed is:

1. A system comprising:
   (a) a catheter assembly including an intravascular imaging device;
   (b) an intravascular blood displacement fluid port;
   (c) a translation device configured to translate the intravascular imaging device; and
   (d) an imaging engine in communication with the intravascular imaging device and the translation device, the imaging engine comprising a computing machine including one or more processors and instructions that when executed by the one or more processors perform the steps of:
      (i) cause the intravascular imaging device to generate a screening image of a section of the patient's blood vessel, the screening image generated while blood is present at the section and prior to introducing a quantity of blood displacement fluid into the patient's blood vessel,
      (ii) identify a sub-section of the patient's blood vessel within the section based on the screening image,
      (iii) calculate a required volume of the quantity of blood displacement fluid based on a physical dimension of the sub-section of the patient's blood vessel, wherein the physical dimension of the sub-section of the patient's blood vessel is calculated based on a cross-sectional area of the sub-section or a length of the sub-section determined from the screening image,
      (iv) cause the intravascular blood displacement fluid port to introduce the quantity of blood displacement fluid into the patient's blood vessel to displace blood within the patient's blood vessel,
      (v) cause the translation device to translate the intravascular imaging device through the sub-section, and
      (vi) cause the intravascular imaging device to generate a blood-displaced image of the sub-section while blood within the sub-section is displaced by the quantity of blood displacement fluid and while the intravascular imaging device is translating through the sub-section.

2. The system of claim 1, wherein the imaging engine further comprises a user interface configured to display the screening image of the section of the patient's blood vessel.

3. The system of claim 2, wherein the imaging engine is configured to identify the sub-section of the patient's blood vessel by receiving a selection of the sub-section via the user interface.

4. The system of claim 1, wherein the imaging engine is configured to identify the sub-section of the patient's blood vessel automatically based on the screening image of the section of the patient's blood vessel.

5. The system of claim 1, wherein the imaging engine is further configured to detect when blood is displaced from the sub-section of the patient's blood vessel and generate the image of the sub-section after the detection of blood displacement.

6. The system of claim 1, wherein the imaging engine is configured to start displacing blood from the sub-section of the patient's blood vessel at substantially the same time as the imaging engine starts generating the blood-displaced image of the sub-section, and the imaging engine is configured to stop displacing blood from the sub-section of the patient's blood vessel at substantially the same time as the imaging engine stops generating the blood-displaced image of the sub-section.

7. The system of claim 6, wherein the imaging engine is configured to start and stop displacing blood from the sub-section of the patient's blood vessel based on a position of the translation device.

8. The system of claim 1, wherein the imaging engine comprises an integrated machine configured to displace blood and to generate the screening image and the blood-displaced image.

9. The system of claim 1, wherein the imaging engine comprises an injection apparatus fluidly connected to the blood displacement fluid port and configured to displace blood.

10. The system of claim 9, wherein the injection apparatus and the intravascular imaging device are configured to communicate and synchronize with one another.

11. The system of claim 9, wherein the injection apparatus comprises a manual injection apparatus.

12. The system of claim 1, wherein the sub-section of the patient's blood vessel is less than all of the section of the patient's blood vessel.

13. The system of claim 1, wherein the intravascular imaging device comprises an IVUS imaging probe.

14. The system of claim 1, wherein the blood displacement fluid comprises contrast media.

15. The system of claim 1, wherein the blood displacement fluid comprises saline.

16. A non-transitory computer-readable storage article comprising computer-executable instructions stored thereon to cause at least one programmable processor to:
   (a) cause an intravascular imaging device to generate a screening image of a section of a patient's blood vessel using an intravascular imaging device, the screening image generated while blood is present at the section and prior to introducing a quantity of blood displacement fluid into the patient's blood vessel;
   (b) identify a sub-section of the patient's blood vessel within the section based on the screening image;
   (c) calculate a required volume of the quantity of blood displacement fluid based on a physical dimension of the sub-section of the patient's blood vessel, wherein the physical dimension of the sub-section of the patient's blood vessel is calculated based on a cross-sectional area of the sub-section or a length of the sub-section determined from the screening image;
   (d) cause an intravascular blood displacement fluid port to introduce the quantity of blood displacement fluid into the patient's blood vessel to displace blood within the patient's blood vessel;
   (e) cause a translation device to translate the intravascular imaging device through the sub-section; and
   (f) cause the intravascular imaging device to generate a blood-displaced image of the sub-section while blood within the sub-section is displaced by the quantity of blood displacement fluid and while the intravascular imaging device is translating through the sub-section.

17. The article of claim 16, further comprising instructions to cause the programmable processor to display the screening image of the section of the patient's blood vessel on a user interface.

18. The article of claim 17, wherein the instructions to cause the programmable processor to identify the sub-section of the patient's blood vessel comprise instructions to cause the programmable processor to receive a selection of the sub-section via the user interface.

19. The article of claim 16, wherein the instructions to cause the programmable processor to identify the sub-section of the patient's blood vessel are to be performed by the programmable processor automatically based on the screening image of the section of the patient's blood vessel.

20. The article of claim 16, further comprising instructions to cause the programmable processor to detect when blood is displaced from the sub-section of the patient's blood vessel and to generate the image of the sub-section after the detection of blood displacement.

21. The article of claim 16, further comprising instructions to cause the programmable processor to cease displacing blood from the sub-section of the patient's blood vessel after the image of the sub-section is generated.

22. The article of claim 16, further comprising instructions to cause the programmable processor to synchronize the displacement of blood within the patient's blood vessel with the generation of the blood-displaced image of the sub-section of the patient's blood vessel by starting displacement of blood from the sub-section of the patient's blood vessel at substantially the same time as starting generation of the blood-displaced image of the sub-section, and by stopping displacement of blood from the sub-section of the patient's blood vessel at substantially the same time as stopping generation of the blood-displaced image of the sub-section.

23. The article of claim 22, wherein the instructions to cause the programmable processor to synchronize the displacement of blood within the patient's blood vessel with the generation of the blood-displaced image of the sub-section of the patient's blood vessel are based on a position of the intravascular imaging device.

24. The article of claim 16, wherein the sub-section of the patient's blood vessel is less than all of the section of the patient's blood vessel.

25. The article of claim 16, wherein the intravascular imaging device comprises an IVUS imaging probe.

26. The article of claim 16, wherein the blood displacement fluid comprises contrast media.

27. The article of claim 16, wherein the blood displacement fluid comprises saline.

28. A system comprising:
   (a) a catheter assembly including an intravascular imaging device;
   (b) an intravascular blood displacement fluid port; and
   (c) an imaging engine in communication with the intravascular imaging device, the imaging engine comprising a computing machine including one or more processors and instructions that when executed by the one or more processors perform the steps of:
      (i) cause the intravascular imaging device to generate a screening image of a section of the patient's blood vessel, the screening image generated while blood is present at the section and prior to introducing blood displacement fluid into the patient's blood vessel,
      (ii) identify a sub-section of the patient's blood vessel within the section based on the screening image,
      (iii) calculate a volume of blood displacement fluid based on a physical dimension of the sub-section of the patient's blood vessel determined from the screening image,
      (iv) cause the intravascular blood displacement fluid port to introduce the calculated volume of blood displacement fluid into the patient's blood vessel to displace blood within the patient's blood vessel, and
      (v) cause the intravascular imaging device to generate a blood-displaced image of the sub-section while blood within the sub-section is displaced by the calculated volume of blood displacement fluid.

29. The system of claim 28, wherein the imaging engine further comprises a user interface configured to display the screening image of the section of the patient's blood vessel.

30. The system of claim 29, wherein the imaging engine is configured to identify the sub-section of the patient's blood vessel by receiving a selection of the sub-section via the user interface.

31. The system of claim 28, wherein the imaging engine is configured to identify the sub-section of the patient's blood vessel automatically based on the screening image of the section of the patient's blood vessel.

32. The system of claim 28, wherein the imaging engine is further configured to detect when blood is displaced from the sub-section of the patient's blood vessel and generate the image of the sub-section after the detection of blood displacement.

33. The system of claim 28, wherein the imaging engine is configured to start displacing blood from the sub-section of the patient's blood vessel at substantially the same time as the imaging engine starts generating the blood-displaced image of the sub-section, and the imaging engine is configured to stop displacing blood from the sub-section of the patient's blood vessel at substantially the same time as the imaging engine stops generating the blood-displaced image of the sub-section.

34. The system of claim 28, wherein the imaging engine comprises an injection apparatus fluidly connected to the blood displacement fluid port configured to displace blood.

35. The system of claim 34, wherein the injection apparatus and the intravascular imaging device are configured to communicate and synchronize with one another.

36. The system of claim 34, wherein the injection apparatus comprises a manual injection apparatus.

37. The system of claim 28, wherein the sub-section of the patient's blood vessel is less than all of the section of the patient's blood vessel.

* * * * *